US006075020A

United States Patent [19]
Cincotta et al.

[11] Patent Number: 6,075,020
[45] Date of Patent: *Jun. 13, 2000

[54] METHOD OF REGULATING IMMUNE FUNCTION

[75] Inventors: Anthony H. Cincotta; Albert H. Meier, both of Andover, Mass.

[73] Assignees: The General Hopital Corporation, Baton Rouge, La.; The Board of Supervisors of Louisiana State University and Agricultural and Mechanical College, Boston, Mass.

[*] Notice: This patent is subject to a terminal disclaimer.

[21] Appl. No.: 09/204,839

[22] Filed: Dec. 3, 1998

Related U.S. Application Data

[63] Continuation of application No. 08/780,727, Jan. 8, 1997, Pat. No. 5,872,127, which is a continuation of application No. 08/271,881, Jul. 7, 1994, Pat. No. 5,696,128.

[51] Int. Cl.$^7$ ............................. A01N 43/42; A61K 31/44
[52] U.S. Cl. ..................................... 514/224.8; 514/226.2; 514/288; 514/323; 514/415; 514/419; 514/619; 514/648
[58] Field of Search ............................. 514/224.8, 226.2, 514/288, 323, 415, 419, 619, 648

[56] References Cited

U.S. PATENT DOCUMENTS

| | | | |
|---|---|---|---|
| 4,310,535 | 1/1982 | Pierpaoli | 424/273 R |
| 4,665,086 | 5/1987 | Short et al. | 514/416 |
| 5,028,591 | 7/1991 | Edwards et al. | 514/12 |
| 5,145,837 | 9/1992 | Feyen et al. | 514/16 |
| 5,344,832 | 9/1994 | Cincotta et al. | 514/288 |
| 5,519,047 | 5/1996 | Shelby et al. | 514/419 |
| 5,696,128 | 12/1997 | Cincotta et al. | 514/284 |
| 5,872,127 | 2/1999 | Cincotta et al. | 514/288 |

FOREIGN PATENT DOCUMENTS

| | | |
|---|---|---|
| 0 308 197 A2 | 3/1989 | European Pat. Off. . |
| 37 19 687 A1 | 12/1988 | Germany . |
| 2 192 541A | 1/1988 | United Kingdom . |
| WO 94/22451 | 10/1994 | WIPO . |

OTHER PUBLICATIONS

Barnett et al., *Postgraduate Med. J.*, 56:11–14, 1980.
Berczi, I. et al., *Acta Endocrinologica*, 98:506–513, 1980.
Berczi, I., *Dev. Comp. Immunol.*, 13:329–341, 1989.
Bernton, E.S. et al., *Science*, 239:401–4, 1989.
Besedovsky, H.O. et al., *J. Immunol.*, 135:750s–4s, 1985.
Blalock, J.E., *Physiol. Rev.*, 69:1–32, 1989.
Blizhakov, *J. Med., N.Y.*, 1980, 11(2/3): 81–105.
Folomeev et al., *Biological Abstracts*, vol. 90, abstract No. 75731, Ter Arkh, 62:62–63, 1990.
Gala, R.R., *Proc. Soc. Exp. Biol. Med.* 198:513–27, 1991.
Gutierrez, M.A., *Rev. Rhum. Fr. Ed.*, 1994, 61:278–85.
Hedner et al., *Am. J. Ophthalmology*, Oct. 1985, 618–19.
Holaday, J.W., "Neuroendocrine—Immune Interaction", 1991, 69 (Suppl. XXVI): 13–19.
Jara et al., *Ame. J. of the Med. Sci.*, 303:222–226, Apr. 1992.
Jara et al., *Semin. Arthritis Rheum.*, 5:273–284, 1991.
Kukhtevich et al., *The Genuine Article*, abstract No. FX734, Terapevtichdkii Ardhiv, 63:99–101, 1991.
Lissoni et al., *Eur. J. Cancer*, 30:167–170, 1994.
Lissoni et al., *Oncology*, 51:344–347, 1980.
Lissoni et al., *Oncology*, 52:163–166, 1995.
López–Korpovitch et al., *AJRI*, 1994, 31:32–39.
Mattsson et al., *Clin. Exp. Immunol.*, 85:41–47., 1991.
McMurray, R., et al., *J. Immunol.* 147:3780–7, 1991.
Meier et al., *Experientia 48*, 148–153, 1992.
Neri et al., *Cancer*, 73:3015–3019, 1994.
Nicoletti, I. et al., *J. Reprod. Immunol.*, 15:113–121, 1989.
Parraquez et al., *J. Dev. Physiol.* (1991) 16(2): 57–62.
Reder, A.T. and Lowy, M.T., *J. Neurobiological Sci.*, 117:192–196, 1992.
Reber, P.M., *Am J. Med.*, 1993 95 (6): 637–644.
Regelson et al., *Cancer Investigation*, 5:379–385, 1987.
Reichlin, S., *NEJM* 329:1246–53, 1993.
Rovensky, J. et al., *Int. J. Immunopharmac.*, 13:267–272, 1991.
Vidaller, A. et al., *Clin. Immunol. Immunopathol*, 38:337–43, 1986.
Vidaller, A. et al., *J. Clin. Immunol.*, 12:210–5, 1992.
Dijkstra et al., Trends Pharmacol. Sci., 14:124–129, 1993.

*Primary Examiner*—Johann Richter
*Assistant Examiner*—Rosalynd Keys
*Attorney, Agent, or Firm*—Darby & Darby

[57] ABSTRACT

Disclosed herein is a method of treating an immune system dysfunction in a mammal by administering a prolactin reducer and a prolactin enhancer at a predetermined time or times.

18 Claims, 17 Drawing Sheets

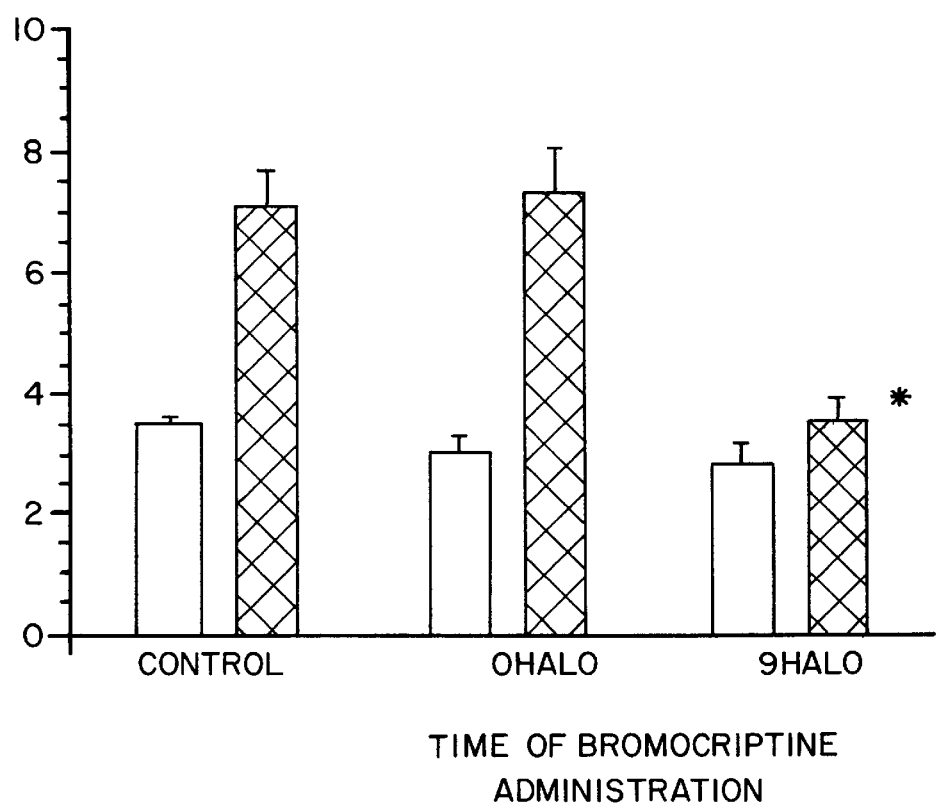

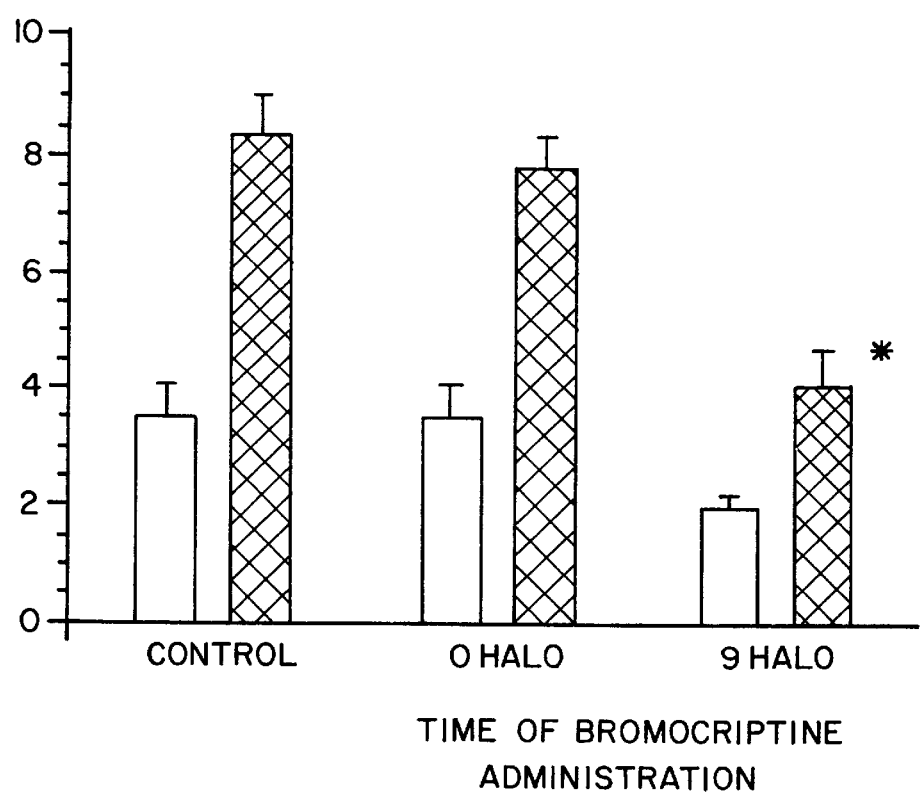

METHOD OF REGULATING IMMUNE FUNCTION

BACKGROUND OF THE INVENTION

This is a continuation of application Ser. No. 08/780,727 filed Jan. 8, 1997 (now U.S. Pat. No. 5,872,127) which is a continuation of application Ser. No. 08/271,881 filed Jul. 7, 1994 (now U.S. Pat. No. 5,696,128).

FIELD OF THE INVENTION

This invention relates to methods for rectifying or ameliorating abnormal responses of the mammalian immune system, and modifying normal responses of the mammalian immune system. More particularly, this invention relates to methods employing the alteration of prolactin rhythms as a method of adjusting mammalian immune response.

PROLACTIN AND IMMUNITY

The importance of neuroendocrine regulation of immunity has become increasingly evident during the past decade (Besedovsky, H. O. et al., J. Immunol. 135:750s–754s, 1985; Blalock, J. E., Physiol. Rev. 69: 1–54, 1989; Berozi, I., *Dev. Comp. Immunol.* 13:329–341, 1989). Much of this interest has focused on the anterior pituitary hormone prolactin, which has been reported to have potent, albeit inconsistent and often conflicting, effects on immune activity (Gala, R. R., *Proc. Soc. Exp. Biol. Med.* 198:5–13, 1991; Nicoletti, J. et al., *Reprod. Immunol.* 15:113–121, 1989; Vidaller, A., et al., *Clin. Immunol. Immunopathol.* 38:337–343, 1986; Gerli, R. et al., *Clin. Immunol.* 7:463–470, 1987).

The role of prolactin in immunity is exemplified by studies demonstrating exogenous prolactin-induced restoration of immune competence in hypophysectomized mammals (Gala, R. R., *Proc. Soc. Exp. Biol. Med.* 198:5–13, 1991; Bercal, I. et al., *Acta Endocrinol.* 98:506–513, 1981). In intact animals, prolactin administration has been associated with numerous immunological effects including stimulation of cellular or antibody responses, as well as stimulation of various immune system upregulating substances such as IL-2 (both IL-2 production and IL-2 receptor expression); enhancement of lymphocyte number, activity and mitogenic responses; and augmentation of macrophage cytotoxicity (Gala, R. R., *Proc. Soc. Exp. Biol. Med.* 198:5–13, 1991; Bernton, E. W. et al., *Science* 239:401–404, 1988; Rovensky, J. et al., *Int. J. Immuno. Pharmac.* 13:267, 1991.)

Other lines of evidence reveal an association between hyperprolactinemia (i.e. elevated levels of circulating endogenous prolactin) which is due to natural, pathological, pharmaceutical, or stress conditions, and states of immune dysfunction, such as immunosuppression or autoimmune diseases. The autoimmune diseases for which exacerbative associations with prolactin have been observed in the past include rheumatoid arthritis, systemic lupus erythematosus (SLE) and multiple sclerosis. Nicoletti, J. et al., *Reprod. Immunol.* 15:113–121, 1989; Vidaller, A., et al., *Clin. Immunol. Immunopathol.* 38:337–343, 1986; Gerli, R. et al., *Clin. Immunol.* 7:463–470, 1987; McMurray, R. et al., *J. Immunol.* 147:3780, 1991.

In light of these apparently conflicting results, (increased prolactin level-associated augmentation of allo-immune response, exacerbated auto-immune response, and immunosuppression) the effects of elevated blood prolactin levels on the immune system have been far from clear.

In recent years, research has focused on improving the ability of the immune system to combat various diseases including malignancies. Experimental evidence that major histocompatibility antigens have an important role in host defenses against the development and spread of tumors has been rapidly accumulating.

Another line of research has specifically focused on suppression of autoimmune diseases, which are characterized by the inability of the immune system to recognize self tissue as "self" and by the mounting of an immune response against self tissue as though it were a foreign antigenic substance.

Yet another area of intensive immunological research is focused on various immunodeficiencies including AIDS. Despite intense research however, progress is slow and the immune mechanisms involved are proving elusive.

Numerous potential immunomodulatory agents are under current investigation by third parties for clinical usefulness. These agents include biologically derived compounds such as interferons and interleukins (and synthetic compounds such as isoprinosine and pyrimidinones). Although interferons and other cytokines and lymphokines are naturally occurring substances, their clinical use (which has involved administration by injection) has not been consistently beneficial (and/or the favorable results have been short-lived). Furthermore, cytokine and lymphokine therapies are most often accompanied by severe side effects such as toxicity and fever.

Accordingly, there is a need in the field of immunology for agents which modify pathological immune system responsiveness and regulate the endogenous production of substances which are in turn native immune system regulators. Use of such agents to "re-program" the immune system: (i) would improve host resistance to infection and ability to combat existing infections; (ii) overcome immunosuppression, abate immunodeficiency, and improve immunity against tumors and restore normal immune function; and (iii) prevent or suppress autoimmunity and restore normal immune function.

PROLACTIN AND CIRCADIAN RHYTHMS

Research has demonstrated that circadian rhythms play important roles in regulating prolactin activities and vice versa.

Publications such as Meier, A. H., *Gen. Comp. Endocrinol.* 3(Suppl 1):488–508, 1972; Meier, A. H., *Trans. Am. Fish. Soc.* 113:422–431, 1984; Meier, A. H. et al., *Current Ornithology II* (ed Johnston R. E.) 303–343, 1984; Cincotta, A. H. et al., *J. Endocrinol.* 120:385–391, 1989; Meier, A. H., *Amer. Zool.* 15:905–916, 1975; Meier, A. H., *Hormonal Correlates of Behavior* (eds. Eleftherton and Sprott) 469–549, 1975 illustrate how circadian rhythms regulate prolactin activities. The resulting daily variations in responsiveness of various cell types to prolactin have a primary role in regulating numerous physiological processes, including fat storage, lipogenic responsiveness to insulin, migratory behavior, metamorphosis, reproduction, growth, pigeon cropsac development and mammary development (Meier, A. H., *Gen. Comp. Endocrinol.* 3(Suppl 1):488–508, 1972; Meier, A. H., *Amer. Zool.* 15:905–916, 1975; Meier, A. H. et al., *Science* 173:1240–1242, 1971). In regulating one of the foregoing physiological activities, prolactin may be observed to produce a stimulatory or an inhibitory effect on a given activity, or to have no effect on it. These varying effects have recently been shown in animals to be a function of the time of the daily endogenous peak (i.e. acrophase) of the rhythm of plasma prolactin concentration or a function of the time of daily injection of exogenous hormone (or of a substance that increases prolactin levels) or of the relation between endogenous peak and any induced peak. Furthermore, high levels of prolactin restricted to a discreet daily interval have a much greater physiologic (e.g. metabolic) effect in animals than do constant high levels throughout a day (Cincotta, A. H. et al., *Horm. Metab. Res.* 21:64–68, 1989; Borer, K. T. in *The Hamster: Reproduction and Behavior* (ed. Siegel, H. I.) 363–408, 1985). Such findings demonstrate the existence of daily response rhythms to prolactin by certain types of cells.

The first demonstration of a daily variation in physiological responsiveness to any hormone was the dramatic variation in fattening responsiveness to prolactin in the white-throated sparrow (Meier, A. H. et al., *Gen. Comp. Endocrinol.* 8:110–114, 1967). Injections at midday of a 16-hour daily photoperiod stimulated 3-fold increases in body fat levels, whereas injections given early in the photoperiod reduced fat stores by 50%. Such daily variations in fattening responses to prolactin were subsequently demonstrated in numerous species of all the major vertebrate classes (Meier, A. H., *Amer. Zool.* 15:905–916, 1975; Meier, A. H., *Hormonal Correlates of Behavior* (eds. Eleftherton and Sprott) 469–549, 1975) indicating the fundamental nature of such a temporal organization. The fattening response rhythm persists under constant light conditions (Meier, A. H. et al., *Proc. Soc. Exp. Biol. Med.* 137:408–415, 1971) indicating that it, like many other endogenous daily variations, is a circadian rhythm.

Additional studies have demonstrated that circadian rhythms have primary roles in regulating numerous physiologic activities such as, lipid metabolism and body fat stores (Meier, A. H. et al., *Current Ornithology II* (ed Johnston R. E.) 303–343, 1984; Meier, A. H., *Amer. Zool.* 15:905–916, 1975; Meier, A. H., *Hormonal Correlates of Behavior* (eds. Eleftherton and Sprott) 469–549, 1975; Meier, A. H. et al., *J. Am. Zool.* 16:649–659, 1976); Cincotta et al., *Life Sciences* 45:2247–2254, 1989; Cincotta et al., *Ann. Nutr. Metab.* 33:305–14, 1989; and Cincotta et al., *Horm. Metabol. Res.* 21:64–68, 1989. These experiments showed that an interaction of circadian rhythms of liporegulatory hormones (stimuli) and of circadian responses to these hormones (in target cells) determines amount of lipogenesis and fat storage. Thus, high plasma concentrations of prolactin (which serves as the stimulus) occur during the daily interval of maximal fattening responsiveness to prolactin in fat animals, but occur at other unresponsive times of day in lean animals (Meier, A. H., *Amer. Zool.* 15:905–916, 1975; Meier, A. H., *Hormonal Correlates of Behavior* (eds. Eleftherton and Sprott) 469–549, 1975; Speiler, R. E. et al., *Nature* 271:469–471, 1978). Similarly, plasma insulin (which acts as the stimulus) levels are highest during the daily interval of greatest hepatic lipogenic response to insulin in obese hamsters, but at a different time of day in lean hamsters (deSouza, C. J. et al., *Chronobiol. Int.* 4:141–151, 1987; Cincotta, A. H. et al., *J. Endocr.* 103:141–146, 1984). The phase relationships of these stimulus and response rhythms are believed to be expressions of neural circadian centers which in turn can be reset by neurotransmitter agents and hormone injections (including prolactin) to produce either fat or lean animals (Meier, A. H., *Trans. Am. Fish. Soc.* 113:422–431, 1984; Meier, A. H. et al., *Current Ornithology II* (ed Johnston R. E.) 303–343, 1984; Cincotta, A. H. et al., *J. Endocrinol.* 120:385–391, 1989; Emata, A. C. et al., *J. Exp. Zool.* 233:29–34, 1985; Cincotta, A. H. et al., *Chronobiol. Int'l* 10:244–258, 1993; Miller, L. J. et al., *J. Interdisc. Cycles Res.* 14:85–94, 1983). Accordingly, timed prolactin administration or enhancement acts directly upon tissues (e.g. liver in lipogenesis) undergoing circadian rhythms of responsiveness to the hormone to produce daily variations in net physiologic effects (Cincotta, A. H. et al., *Horm. Metab. Res.* 21:64–68, 1989) and acts indirectly by resetting one of the circadian neuroendocrine oscillations of a multi-oscillatory circadian pacemaker system to establish different phase relations between the multiple circadian (neural, hormonal, and tissue) expressions that control lipid metabolism (Meier, A. H., *Trans. Am. Fish. Soc.* 113:422–431, 1984; Meier, A. H. et al., *Current Ornithology II* (ed Johnston R. E.) 303–343, 1984; Cincotta, A. H. et al., *J. Endocrinol.* 120:385–391, 1989; Emata, A. C. et al., *J. Exp. Zool.* 233:29–34, 1985; Cincotta, A. H. et al., *Chronobiol. Int'l* 10:244–258, 1993; Miller, L. J. et al., *J. Interdisc. Cycles Res.* 14:85–94, 1983).

The present inventors have previously shown that prolactin, or substances that affect circulating prolactin levels, also affect circadian rhythms and in fact can be used to modify such rhythms (so that they more closely resemble the rhythms of lean, healthy, young individuals of the same sex) and to reset such rhythms (so that they persist in the modified condition). See, e.g. U.S. patent applications Ser. Nos. 08/158,153 [07850], 07/995,292 [07788], 07/719,745 [17849], 07/999,685 [07848] and 08/171,569. This prior work by the present inventors has been clinically tested in humans afflicted with various metabolic disorders (obesity, diabetes and others) with very favorable results.

In particular, in U.S. patent application Ser. No. 07/995,292, and in its continuation-in-part Ser. No. 08/264,558, filed Jun. 23, 1994, the present inventors disclose a method for the reduction in a subject, vertebrate animal or human, of body fat stores, and reduction of at least one of insulin resistance, hyperinsulinemia, and hyperglycemia, and other metabolic diseases, especially those associated with Type II diabetes. More specifically, the foregoing application discloses methods for: (i) assessing the daily prolactin level cycles of a normal (healthy) human or vertebrate animal (free of obesity, disease or other disorder); (ii) diagnosing aberrant daily prolactin level cycles of a human or vertebrate animal; and (iii) determining the appropriate adjustments that need to be made to normalize such aberrant prolactin level cycles. This method involves the administration of at least one of a prolactin reducer and/or a prolactin enhancer at a first predetermined time (or times) within a 24-hour period (if only a prolactin reducer is administered) and/or at a second predetermined time (or times) of a 24-hour period (if a prolactin enhancer is administered). This therapy, when continued for several days, weeks or months, results in the long-term adjustment of aberrant or abnormal prolactin level cycles so that they conform to (or simulate) normal prolactin level cycles. This benefit persists over the long-term even after cessation of therapy. As a result, aberrant physiological parameters associated with various metabolic disorders are restored to normal levels or are modified to approach normal levels. Although this method is applied to all persons having aberrant prolactin levels during at least a portion of a 24-hour period, it does not mention the possibility of applying it to persons suffering from immune dysfunction.

Thus, the mutual dependence of prolactin and circadian rhythms and particularly the time-sensitivity of such dependence has not previously been correlated with immune function or dysfunction. The present inventors postulated (i) a similar daily variation of the response of the immune system to prolactin and (ii) an ability of timed, induced variations in prolactin levels to modulate immune responses by influencing production of naturally occurring immune system (up- or down-) regulators. Experimental confirmation of these postulates gave rise to the present invention, and resolved the apparent conflicts in the effects of prolactin on immunity.

SUMMARY OF THE INVENTION

One aspect of the present invention is directed to a method of ameliorating or rectifying immune system abnormalities in a mammal in need of such treatment. The method involves the administration to the mammal of a prolactin reducer and/or enhancer at a predetermined time or times during a 24-hour period that results in modification of the mammal's abnormal prolactin profile so that it approaches or conforms to the prolactin profile of a young healthy mammal of the same species.

Another aspect of the present invention is directed to a method of ameliorating or rectifying immune system abnormalities on a long-term basis by continuing the foregoing timed administration(s) of the prolactin reducer and/or enhancer until the altered prolactin rhythm of the subject is reset and persists in this reset condition for an extended period of time even after cessation of therapy, resulting in persistence of the improvement of immune system abnormalities.

Yet another aspect of the invention is directed to a method of augmenting (upregulating) immune response in a mammal (e.g., for the purpose of increasing the subject's ability to mount an immune response against infection). The method involves the timed administration of a prolactin reducer and/or enhancer at a time or times (respectively) at which reducing (or enhancing) the subject's plasma prolactin levels would enhance the subject's ability to mount an immune response. This method may also be practiced on subjects having a normal immune system.

Thus, the present invention is directed to adjusting the phase relationship between the circadian rhythms for prolactin and for one or more immune responses. The invention involves normalizing (or resetting) the circadian rhythm for prolactin to resemble that of a healthy young subject. The invention also involves manipulating the circadian rhythm for prolactin to bring it in such a phase and amplitude relation with the immunologic responsiveness to prolactin as to exert an amplifying effect on a predetermined aspect of the immune response.

"Immune dysfunction" or "immune abnormality" means individually or collectively a state of immunodeficiency or immunosuppression (marked by inability or compromised ability to mount an immune response against a pathogen or other affliction such as a tumor) and/or a state of mistargeted immune activity such as autoimmunity. Immunodeficiency and immunosuppression include situations where a subject has reduced ability to mount a T-cell response or a B-cell response (as evidenced for example by reduced mixed lymphocyte reaction, reduced delayed-type hypersensitivity or reduced T- or B-cell proliferation to a stimulus); or has reduced ability to produce cytokines or lymphokines or antibodies; or exhibits reduced expression of lymphokine receptors or reduced antigen-presenting ability (as evidenced for example by reduced expression of Class I or Class II Major Histocompatibility Complex). Such compromised ability to mount an immune response can be the result of congenital or acquired immunodeficiency or the result of chemotherapy or radiation, or other drug-induced immunosuppression. Consequently, a rectification or amelioration of immune dysfunction is the total or partial restoration of one or more of the foregoing immune responses.

"Prolactin reducer" is a substance or composition that has the ability to lower circulating prolactin levels upon administration to a mammal; "prolactin enhancer" is a substance or composition that has the ability to raise circulating prolactin levels, and includes prolactin itself.

Prolactin reducers and prolactin enhancers are referred to collectively as "prolactin modulators".

"Prolactin profile" of a subject is a depiction of circulating prolactin levels and their variation over all or part of a 24-hour period, and therefore an expression of all or part of the subject's plasma prolactin daily rhythm.

"Healthy" is a young, lean subject free of disease including malignancies, immune system dysfunctions and metabolic abnormalities. A healthy subject is one with a normal prolactin profile, i.e., a prolactin profile that does not depart from the baseline of that subject's species and sex by more than one standard error of the mean (SEM). The normal or baseline profile for healthy male and female humans is depicted in FIG. 1.

In order to avoid "false positives" a subject will not generally be considered to have an abnormal prolactin profile unless:

(a) the subject's daytime blood prolactin level is at least 1 SEM higher than the baseline at two (or more) time points during daytime spaced apart by at least one and preferably by at least two hours; or (b) the subject's daytime blood prolactin level is at least 2 SEM higher than the baseline at one time point during daytime; or (c) the subject's night time blood prolactin level is at least 1 SEM below the base line at two (or more) spaced apart time points (as in (a)); or (d) the subject night time blood prolactin level is at least 2 SEM below the base line at one time point during night time.

The human male and female baselines are depicted in FIG. 1. One SEM during waking hours (07:00–22:00) is about 1–2 ng/ml for males and about 1–3 ng/ml for females; one SEM during night time (22:00–07:00) is about 3 ng/ml for males and about 3–6 ng/ml for females.

The characteristics of the prolactin level daily rhythm or profile that are to be approached or conformed in humans include achieving low prolactin levels (2–7 ng/ml of plasma) for males and 2–10 ng/ml for females) during most or all of the time period between 07:00 and 22:00 h.

Ideally, a peak prolactin level should also be achieved between the hours of 22:00 and 07:00 (preferably between 1:00 and 4:00) (the peak should be at least 10 ng/ml and most preferably between 10–15 ng/ml for males and at least 15 ng/ml and preferably between 15 and 25 ng/ml for females).

Advantages of the present invention include:

upregulation of immune responses when needed to combat disease;

restoration of normal immune responses (abatement of autoimmunity, immunodeficiency).

The benefits of the present invention may persist long-term even after cessation of the administration of prolactin modulators.

Other features and advantages of the present invention will be apparent from the following description taken in conjunction with the accompanying drawings.

BRIEF DESCRIPTION OF THE DRAWINGS

FIGS. 6A and 6B are the same type of diagrams as FIG. 3 but showing the relationship between MLR and time of day of a prolactin reducer administration; FIG. 6A: 200 μg bromocriptine; FIG. 6B: 50 μg bromocriptine.

DETAILED DESCRIPTION OF THE INVENTION

Figure 1:
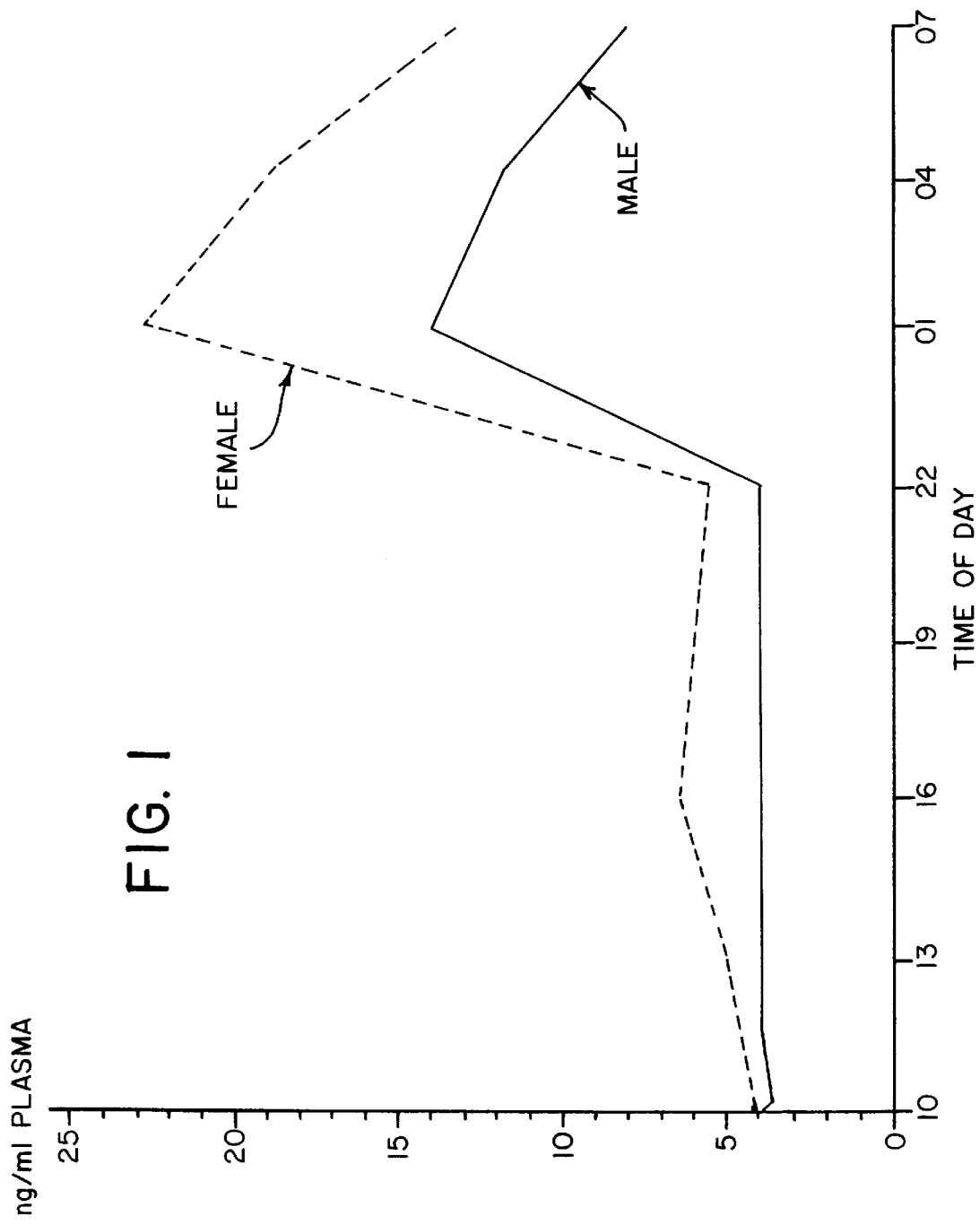
FIG. 1 is the baseline prolactin daily rhythm or profile curve for healthy males and females.

All patents, patent applications, and literature references discussed in this specification are hereby incorporated by reference. In case of conflict, the present disclosure controls.

Effects of Prolactin Modulation on Immune Responses

The alteration of prolactin levels in a subject having a normal immune system (either by administering prolactin, or by administering substances that alter prolactin blood levels) has been found to augment or reduce a subject's ability to mount an immune response to a given challenge. Whether the effect on the immune response is stimulatory or suppressive is dependent on the time of day the alteration of the prolactin levels occurs and on the nature of the alteration. Thus, increasing the plasma levels of the hormone at or near a time when cellular responsiveness to high prolactin is at its peak, in mice preferably about 10–12 hours after light onset (HALO), normal immune responses (and immune responses to alloantigens) are augmented. Conversely, decreasing prolactin plasma levels at or near the peak of responsiveness, in mice 4–12 HALO, preferably 10–12 HALO, suppresses immune response. On the other hand, causing the circulating prolactin levels to increase at a time when cellular responsiveness to prolactin is at its lowest, in mice preferably at approximately light onset (20–24 HALO and 0–3 HALO; preferably 22–24 HALO and 0–2 HALO), immune responses are often (but not always) suppressed.

The experimental data described herein show that prolactin injections (or prolactin enhancer administration) 9–12 HALO cause an increase in the mouse mixed lymphocyte response (MLR) to alloantigens and an increase in the proliferation of nonstimulated mouse splenocytes as compared to naive controls. Prolactin injections (or prolactin enhancer administration) made 16–24 HALO did not have a significant effect on MLR. Prolactin injections (or enhancer administration) at light onset resulted in significant inhibition of mouse immune responsiveness (as measured by MLR) as compared to naive controls. These results indicate that the effect of in vivo prolactin modulation of in vitro immune responses to foreign antigen is time-of-day dependent. In vivo response to antigen as measured by delayed-type hypersensitivity (DTH) experiments is also described herein. As with the MLR above, prolactin injections made at light onset often (but not always) inhibited the foot pad swelling response, indicating that prolactin caused a reduced immune response; however, prolactin administration at 10 HALO was significantly stimulatory relative to control.

A time of day dependent role for prolactin in immune responses is also indicated by results of experiments on mice which decrease prolactin blood levels (by administration of a prolactin reducer) during specific daily intervals of daily immune responsiveness to exogenous prolactin (i.e. during an interval about 9–12 HALO in mice and another interval about 0 HALO in mice). Dose-response studies with bromocriptine, a D2 dopamine agonist which inhibits endogenous prolactin secretion, indicate that bromocriptine exerted an inhibitory action on the DTH response at 10 HALO but not at 0 HALO. Bromocriptine was also found to be inhibitory for T and B cell proliferative responses to mitogenic stimulation with either concanavalin A (100%; p<0.01) or lipopolysaccharide (47%; p<0.01) respectively, when administered at 10 but not at 0 HALO.

The above in vitro and in vivo immune responses are dependent on mature T cell activation. Thymic hormones are essential for the differentiation of progenitor T cells within the thymus. Moreover, thymic hormones enhance peripheral T cell activity (Baxevanis, C. N. et al., *Immunopharm* 15:73–84, 1988), major histocompatibility complex class II antigen expression (Baxevanis, C. N. et al., *J. Immunol.* 148: 1979–1984, 1992), and augment antigen presenting function (Tzehoval, E. et al., *Immunopharm.* 18:107–113, 1989), all of which can promote MLR and DTH reactivity. Inasmuch as prolactin stimulates thymic epithelial cell proliferation as well as thymic hormone production (Dardenne, M. et al., *Endocrinology* 125:3–12, 1989), prolactin should also have an effect on thymus cell number. Indeed, daily prolactin injections were given to 5 week old mice either at light onset or at 11 HALO for one month. Prolactin treatment at 11 HALO significantly increased thymus cell number relative to controls whereas prolactin injections at light onset did not.

The above results indicate the immunomodulatory effects of prolactin levels and the relationship of cellular responsiveness to exogenous prolactin (or prolactin enhancers or reducers), and the time of day of prolactin reduction or enhancement.

Although the foregoing experiments were conducted in mice, they are dependent on features of the immune system that are common to mammals having a prolactin daily rhythm including humans. These results show that the blood levels of prolactin can be manipulated during predetermined intervals to bring about a desirable effect on the immune system.

According to the method of the present invention, the alteration of prolactin levels of a subject at particular times of day provides methods of improving immune responsiveness of the subject or restoring or augmenting normal immune responses or ameliorating abnormal immune responses. The method may be used to increase the protection of subjects that are immunosuppressed (or even subjects that do not suffer from immunosuppression) against infection. Augmenting the immune response will provide an increased level of protection against invading pathogens such as viruses, bacterial, or fungal infections in susceptible individuals. This method will also be useful in the treatment of individuals who are immunocompromised or immunodeficient independent of the cause. Additional subjects who could benefit from this treatment method include without limitation allograft recipients, surgery patients, allergy sufferers, burn victims, cancer patients receiving chemotherapy or radiation therapy, patients suffering from HIV-infection or a congenital immunodeficiency such as severe combined immunodeficiency (SCID) or DiGeorge Syndrome. Any subject whose immune system has been deregulated (but not completely ablated) by a congenital or clinical condition or by medication will benefit from the present invention. An augmentation in immune responses is also of value in groups sharing common quarters, such as military recruits, summer campers, or disaster victims, or with the aged in nursing homes, who are at a high risk of contracting infections.

The method can also be used to reduce or eliminate damage to a subject caused by a deleterious immune reaction. Specifically, subjects suffering from autoimmune diseases whether such conditions are mediated or dependent on B-cells, T-cells or both. Nonlimiting examples include rheumatoid arthritis, multiple sclerosis, endocrine ophthalmopathy, uveoretinitis, the autoimmune phase of Type 1 diabetes, systemic lupus erythematosus, myasthenia gravis, Grave's disease, glomerulonephritis, autoimmune hepatological disorder, autoimmune inflammatory bowel disease, and Crohn's disease. Subjects suffering from inflammation having immune reaction characteristics (e.g. anaphylaxis, allergic reaction) would also benefit from the present treatment method. This method is also useful in the treatment of recipients of tissue or organ transplants to reduce host-induced allograft rejection.

Use of Prolactin Modulators to Alter Immune Response (a) Adjusting Prolactin Rhythms of Subjects With Immune Dysfunction It is known that young adult healthy mammals of a given species (and sex), e.g. humans (suffering from no hormonal or metabolic disorders or cancer or other infection or ailment) have highly predictable daily prolactin level rhythms or profiles. The baseline curve for healthy human males and females in FIG. 1 is derived from such young healthy individuals.

It is also known that persons suffering from immune dysfunction have abnormal prolactin rhythms. Nicoletti, supra; Vidaller, supra; Gerli, supra; McMurray, supra; Fraga, A. et al., Arthritis Rheum. 32:524, 1989; and Laualle, C., J. Rheumatol. 14:266, 1987.

The phase relationship between the daily peaks of the stimulus (plasma prolactin) rhythm and response (immunocellular rhythm) to prolactin is of critical importance to the status of immune function. Environmental and pharmaceutical factors influencing either of these rhythms can be expected to impact immune function. Furthermore, phase shifts in either or both of these rhythms may be associated with immunologic disorders, as well as cancer (Bartsch, C. et al., J. Pineal Res. 2:121–132, 1985; Bartsch, C. et al., Cancer 64:426–433, 1989).

For example, persons with autoimmune disease commonly have hyperprolactinemia during the day, especially in AM after dawn at which time, in humans, it is believed that the excess (above baseline) prolactin deregulates immune function. By adjusting (reducing) the daytime prolactin levels of such individuals the deregulation of immune function can be rectified or ameliorated. In terms of the foregoing experiments this would be equivalent to an animal the immune function of which has been deregulated by administration of prolactin, e.g. at zero HALO. The immune function can be restored by administration of a prolactin reducer at zero HALO.

Persons with immune dysfunction thus benefit to a significant extent by adjustment of their prolactin daily rhythms (as expressed by their prolactin profile) to conform to or approach the normal or baseline prolactin curve of FIG. 1. An adjusted profile approaches a normal or healthy profile, if all or a portion of the abnormal profile moves in the correct direction by at least 2 ng/ml.

This adjustment can be accomplished by administration to such individuals of one or both of the following:

a prolactin reducer at a first predetermined time (or at more than one first predetermined time) and in a first amount effective to reduce day time prolactin levels if these levels are too high; and a prolactin enhancer at a second predetermined time (or at more than one second predetermined times) and in a second amount effective to increase night time prolactin levels if these levels are too low.

In general, if a prolactin level altering substance is to be administered, appropriate allowance should be made with respect to the time of administration to permit that substance (depending on its pharmacokinetic properties) to affect prolactin levels such that prolactin levels would be modified during the appropriate time of day. Thus, the prolactin altering substance will be administered as follows:

(a) if prolactin is administered, it will be administered during the time interval that prolactin levels need to be raised;

(b) if a prolactin enhancer other than prolactin is administered, it will be administered during or slightly prior to the time interval when prolactin levels need to be raised (how much prior depends on pharmacokinetic properties: generally 0–3 hours prior will be effective); and (c) if a prolactin reducer is administered it will also be administered during or slightly prior to the time that prolactin levels need to be reduced (again, 0–3 hours prior will be generally effective).

In the method of the present invention, "prolactin enhancer" includes prolactin as well as substances which increase circulating prolactin levels (e.g. by stimulating prolactin secretion). Non-limiting examples of a prolactin enhancer include prolactin; melatonin; dopamine antagonists such as metoclopramide, haloperidol, pimozide, phenothiazine, domperidone, sulpiride and chlorpromazine;

serotonin agonists, i.e., MAO inhibitors, e.g., pargyline, synthetic morphine analogs, e.g., methadone; antiemetics, e.g., metoclopramide; estrogens; and various other serotonin agonists, e.g., tryptophan, 5-hydroxytryptophan (5-HTP), fluoxitane, and dexfenfluramine. Moreover, the non-toxic salts of the foregoing prolactin enhancing compounds formed from pharmaceutically acceptable acids are also useful in the practice of this invention. Metoclopramide has been found particularly useful in the practice of this invention.

Nonlimiting examples of prolactin reducers include prolactin-inhibiting dopamine agonists such as dopamine and certain ergot-related prolactin-inhibiting compounds. Nonlimiting examples of dopamine agonists are 2-bromo-alpha-ergo-criptine; 6-methyl-8beta-carbobenzyloxy-aminoethyl-10-alpha-ergoline; 8-acylaminoergolines, are 6-methyl-8-alpha-(N-acyl)amino-9-ergoline and 6-methyl-8alpha-(N-phenylacetyl)amino-9-ergoline; ergocornine; 9,10-dihydroergocornine; and D-2-halo-6-alkyl-8-substituted ergolines, e.g., D-2-bromo-6-methyl-8-cyanomethylergoline; carbi-dopa and L-dopa; and lisuride. Moreover, the non-toxic salts of the prolactin-reducer compounds formed with pharmaceutically acceptable acids are also useful in the practice of this invention. Bromocriptine, or 2-bromo-alpha-ergocryptine, has been found particularly useful in the practice of this invention.

The modulation of immune responses induced by prolactin enhancers or reducers is expected to be dose-dependent over a range of dosages.

In treating mammals, generally, dosages of the prolactin reducer and/or enhancer, respectively, are each given, generally once a day, generally over a period ranging from about 10 days to about 180 days, but treatment can continue indefinitely (if necessary or desired) for months or even years. The preferred prolactin reducer (accelerated release bromocriptine) is given daily at dosage levels ranging from about 3 micrograms to about 100 micrograms, preferably from about 10 micrograms to about 40 micrograms, per kg of body weight, and the preferred prolactin enhancer (metoclopramide) is given daily at dosage levels ranging from about 5 micrograms to about 200 micrograms, preferably from about 5 micrograms to about 100 micrograms, per kg of body weight per day to modify, or alter, the prolactin profile.

Administration of either or both prolactin altering substances can be continued for a time sufficient to reset the circadian plasma prolactin rhythm to the phase and amplitude modified by administration of the prolactin altering substance, at which time treatment may be discontinued. If the subject suffers a relapse, treatment may be resumed. The time needed for resetting varies but is generally within the range of 30–180 days.

In treating humans, in particular, the prolactin reducer (accelerated release bromocriptine) is generally given at daily dosage levels ranging from about 3 micrograms to about 100 micrograms, preferably from about 10 micrograms to about 40 micrograms, per kg of body weight (typically 0.2–1.5 mg/person/day; preferably 0.8–8 mg). The prolactin enhancer metoclopramide is generally given at daily dosage levels ranging from about 1 micrograms to about 50 micrograms, preferably from about 5 micrograms to about 20 micrograms, per kg of body weight per day. (Per person daily dosages range of metoclopramide are typically 0.5 to 5.0 mg; preferably 0.5 to 2.0 mg.) Such treatment (using one or both types of prolactin altering substances) is typically continued over a period of time ranging from about 10 days to usually about 180 days, resulting in modification and resetting of the immune functions of the patient to that of a lean, young, healthy person, at which time treatment may be discontinued. For some patients (e.g. patients in particularly poor physical condition, or those of an advanced age) it may not be possible to reset their prolactin rhythm within the above time periods and such patients may require a longer, or even continuous, treatment with prolactin enhancers and/or reducers. The dosage and timing information set forth above is designed for bromocriptine and metoclopramide and will have to be altered for other agents using the dosage and timing methodology disclosed herein.

In the practice of this invention, a prolactin reducing compound, and/or a prolactin enhancer are administered daily to a subject preferably orally, or by subcutaneous, intravenous or intramuscular injection. Dermal delivery systems e.g., skin patches, as well as suppositories and other well-known systems for administration of pharmaceutical agents can also be employed. Treatment generally lasts between about 10 and about 180 days on average in humans. The administration of the prolactin reducer and/or prolactin enhancer in this manner will thus reset the phase and amplitude of the neural oscillators that control the immune system to rectify or ameliorate immune function on a long term basis (e.g., several months or years). An improvement or amelioration in immune function can be assessed by observation of partial or total restoration of the ability to mount immune response as described above in connection with the definition of immune dysfunction. In the case of autoimmune disease, an improvement or amelioration can best be assessed by a significant reduction or disappearance of a clinical symptom associated with inflammation caused by the autoimmune disease, for example: joint pain or swelling or stiffness in rheumatoid arthritis; number of major attacks in chronic-relapsing multiple sclerosis; stabilization or improvement of motor function in chronic progressive multiple sclerosis; intestinal inflammation in the case of Chron's disease; and serological measurements (such as antibody to double-stranded DNA, complement components and circulating immune complexes), number and severity of skin flareups or myalgras, arthralgia, leukopenia, or thrombocytopenia for systemic lupus erythematosus. The symptoms which can be used to monitor efficacy of a regimen in autoimmune disease are generally well-known in the art.

Improvement in ability to mount an immune response against infection can also be measured by testing for the infectious agent.

The following more specific guidelines will generally be followed to initially determine bromocriptine administration timing, for a period of treatment of approximately 26 weeks:
a) Week 1 to Week 6.
  First Dosage: If any one of a patient's 07:00, 08:00, 16:00 or 19:00 prolactin levels is equal to or higher than 5.0 ng/ml for males or 7.0 ng/ml for females, then 0.8 mg of accelerated release bromocriptine is administered at 06:00 daily.
  Second Dosage: Beginning in week 3, a second dosage containing 0.8 mg of accelerated release bromocriptine is also administered at 10:30 daily.
b) Week 7 to Week 12.
  First dosage: If any one of the 07:00, 08:00, 16:00, or 19:00 prolactin values is still equal to or higher than 5.0 ng/ml for males or 7.0 ng/ml for females, then 1.6 mg of accelerated release bromocriptine are administered at 06:00. Otherwise, 0.8 mg of accelerated release bromocriptine is administered at 06:00 daily.
  Second Dosage: In addition, if the 19:00 prolactin level is less than or equal to 1.5 ng/ml for males or females then the second dosage of 0.8 mg of accelerated release bromocriptine is administered at 08:30 daily instead of at 10:30. If the 19:00 prolactin level is higher than 1.5 ng/ml for males and females, then the second dosage continues to administered at 10:30 daily.

If the 19:00 prolactin level is less than 1.0 ng/ml for males and females, then there is no administration of second dosage.

c) Week 13 to Week 26. For both first and second dosages the rules are the same set forth for Weeks 7–12, subject to the following:

(i) If either the 16:00 or 19:00 prolactin level is equal to or higher than 5.0 ng/ml for males or 7.0 ng/ml for females, then add an additional 0.8 mg of accelerated release bromocriptine to the first dosage, unless the patient is already receiving 2.4 mg of bromocriptine in total. In that case, add the additional 0.8 mg of accelerated release bromocriptine to the second dosage;

(ii) If the 19:00 prolactin level is lower than 1.5 ng/ml for males or females, then the second dosage time is adjusted by administering it 2 hours earlier; and (iii) If each of the 08:00, 16:00 and 19:00 prolactin levels is less than 1.0 ng/ml for males or females, then subtract 0.8 mg of accelerated release bromocriptine from the second dosage, or, if there is no second dosage, then subtract 0.8 mg of accelerated release bromocriptine from the first dosage. In the vast majority of patients, the first dosage must contain a minimum of 0.8 mg of accelerated release bromocriptine.

The time and amount schedules given above are intended as guidelines for bromocriptine administration and those skilled in the art can further adjust the precise timing and amount of bromocriptine administration based on the actual prolactin profile or key prolactin levels of a patient to be treated. For example, if a patient does not respond (or does not respond adequately) to a given dosage or dosages (e.g. 0.8 mg) it (or they) can be increased (e.g. to 1.6 mg).

When needed, metoclopramide (generally daily dosage range is 0.5–5.0 mg/person; preferred daily dosage range is 0.5–2.0 mg/person) can be administered once about one hour before bedtime.

Of course, the foregoing dosages are subject to optimization and it is expected that there will be minimum and maximum effective dosages. In other words, adjustment of the prolactin rhythm or levels to regulate immune response will occur within a specific dosage range. (This is also illustrated in Example 2 below for downregulation of immune responses using bromocriptine as the prolactin modulator.)

The aspect of the invention directed to a modulation of the immune system by resetting the prolactin level profile of a vertebrate subject (animal or human) having an aberrant prolactin profile to conform to or approach the prolactin profiles for young healthy members of the same species and sex (e.g. the baselines of FIGS. 12 et seq.) involves administration of a prolactin reducers, or a prolactin enhancer, or both, at predetermined dosages and times dictated by the aberrant (pre-treatment) prolactin profile of the subject to be treated. The amounts of prolactin reducers and/or enhancers that are required to bring about this modification are within the same ranges as set forth above, but the time(s) of administration of these prolactin modulator(s) is determined by reference to how much and when the aberrant profile differs from the normal prolactin profile (baseline curve). Methods for determining the amounts and timing of administration are also set forth in our copending U.S. patent application Ser. No. 07/995,292 and its C-I-P, Ser. No. 08/264,558, filed Jun. 23, 1994, both incorporated by reference. A preferred accelerated release bromocriptine dosage form has been disclosed in our copending U.S. patent application Ser. No. 08/171,897 also incorporated by reference.

(b) Augmenting Immune Responses

As illustrated in Examples 1–5, the present invention provides a method for augmenting immune responses (e.g. increased T-cell response or B-cell response etc as described above in connection with the definition of immune dysfunctions) to increase a subject's ability to fight infection. This can be accomplished by administration of prolactin or another prolactin enhancer at a predetermined time during a 24-hour period at which increased bloodstream levels of prolactin enhance immune response.

In mice, prolactin injections or administration of prolactin enhancers were shown to be immunostimulatory during the interval of 4–12 HALO during which time the immune system responds positively to increased prolactin levels.

In treating any mammal having a prolactin daily rhythm in accordance with this aspect of the method of the present invention, the appropriate interval of positive immunoresponsiveness to increased prolactin must first be ascertained. This can be accomplished by experiment similar to those of Examples 1–5. Instead of MLR or DTH measurements, well-known lymphocyte proliferation or lymphocyte activation assays or lymphocyte characterization methods can be used to assess the effect of increased prolactin. Once a time point within the appropriate time interval has been identified, administration of the prolactin enhancer can be undertaken. The time of administration can be further optimized by repeating experiments such as those of Examples 1–5 at time points spaced apart from (e.g. within 3 hours of) a time point where prolactin enhancement has been found to be effective in augmenting immune response.

Ascertaining the effective dosage range as well as the optimum amount is well within the skill in the art. For example, dosages for mammals can be determined by beginning with a relatively low dose (e.g., 0.8 mg bromocriptine or 0.5 mg of metoclopramide), progressively increasing it (e.g. logarithmically) and assessing the immune responses of the mammal according to well-known methods, as detailed in Examples 1–5, below. The optimum dosage will be the one generating the maximum or minimum MLR, DTH response, thymic cell count or other measurement of immune responsiveness. An effective dosage range will be one that causes at least a statistically significant alteration of at least one measurement of immune response.

For mammals, generally the amount of prolactin enhancer to augment immune response will be within the range of 1 to 50 μg/kg/day If the enhancer is prolactin, the range will be 10 to 1000 ng/kg/day For humans, the amounts of prolactin will generally be the same as above; those for domperidone will be 0.17 to 17 mg/kg/day; 5HTP, 1 to 50 mg/kg/day.

Without being bound by theory, it is hypothesized that daily administration of exogenous prolactin or increase of endogenous prolactin levels mediates a coordinated cellular preactivation state which readies cells for immune responsiveness. Prolactin stimulation of lymphocytes induces the activation of ornithine decarboxylase, nuclear protein kinase C, IL-2 production, and IL-2 receptor expression necessary for enhanced responses to foreign antigen (Gala, R. R., *Proc. Soc. Exp. Biol. Med.* 198:5–13, 1991; Russel, D. H., *Trends Pharm. Sci.* 10:40–44, 1989). Since prolactin receptors have been identified on polymorphonucleocytes and macrophages, as well as lymphocytes (Gala, R. R., *Proc. Soc. Exp. Biol. Med.* 198:5–13, 1991), this "preactivation" may serve to target various cell activities enhancing immune responses (e.g. MLR and DTH), including the production of thymic hormones known to stimulate MLR (Baxevanis, C. N. et al., *Immunopharm* 15:73–84, 1988), the production of cytokines (Tzehoval, E. et al., *Immunopharm.* 18:107–113, 1989), and enhancement of antigen-presenting ability by increasing expression of class II MHC (Baxevanis, C. N. et al., *J. Immun.* 148: 1979–1984, 1992) and/or possibly B7 antigens.

Based on previous observations in other physiological systems, the phase (i.e. daily peak) of this immunocellular response rhythm to prolactin may be entrained directly or centrally by other humoral or neural factors. Humoral factors include for example corticosteroid (Meier, A. H., *Trans. Am. Fish. Soc.* 113:422–431, 1984; Meier, A. H. et al., *Current Ornithology II* (ed Johnston R. E.) 303–343, 1984; Cincotta, A. H. et al., *J. Endocrinol.* 120:385–391, 1989). Neural factors include for example dopamine (Emata, A. C. et al., *J. Exp. Zool.* 233:29–34, 1985; Cincotta, A. H. et al., *Chronobiol. Int.* (in press); Miller, L. J. et al., *J. Interdisc. Cycles Res.* 14:85–94, 1983). It should be clarified that the daily variation of immunologic responsiveness to prolactin is distinct from the well-established circadian rhythm of immune activity (Fernandez, J. in *Biologic Rhythms in Clinical and Laboratory Medicine* (eds. Y. Touitou & E. Haus) 493–503, 1992).

The present invention may be better understood by experiments described in the Examples below. These Examples are to be considered illustrative only of the principles of the invention. Further, since numerous modifications and changes will readily occur to those skilled in the art, it is not desired to limit the invention to the exact construction and operation shown and described. Accordingly, all suitable modifications and equivalents may be used and will fall within the scope of the invention and the appended claims.

EXAMPLE 1

TIME OF DAY DEPENDENT EFFECTS OF PROLACTIN ON THE ONE-WAY MIXED LYMPHOCYTE REACTION

Figure 2:
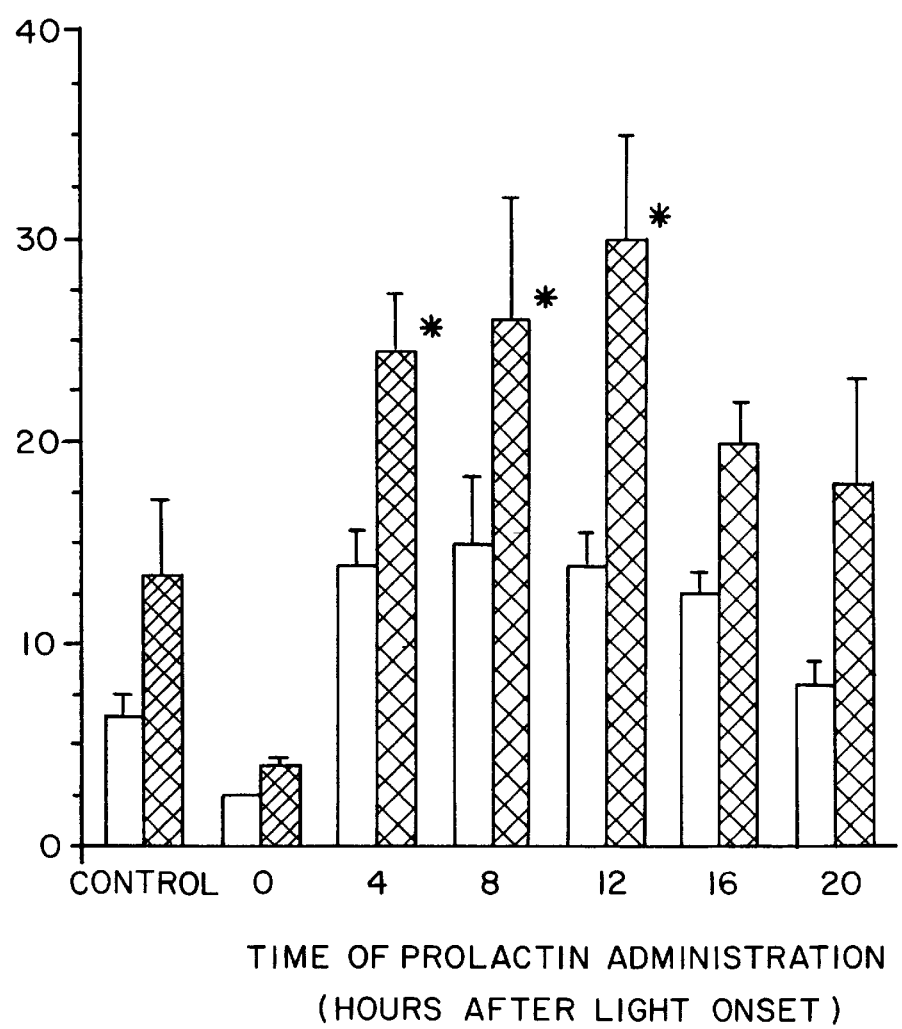
FIGS. 2 and 3 are bar diagrams showing the relationship between mixed lymphocyte reaction (MLR) and time of day of prolactin administration. An asterisk denotes a significant difference from control (p<0.05; Student's t test)

Groups (n=3–6) of adult male BALB/c and C57BL/6 mice (Charles River, Wilmington, Mass.) were maintained from birth on 12 hour daily photoperiods. Ovine prolactin available from Sigma Chemical Co., St. Louis, Mo.) was injected intraperitoneally (1 mg/kg body weight, 20 µg/animal/day for 10 days) at 0/24, 4, 8, 12, 16 or 20 HALO. A control group remained untreated. Individual spleen cells (responder cells) were then obtained from control or experimental mice by standard methods, erythrocytes lysed, and the splenocytes were resuspended in RPMI 1640 (Gibco, Grand Island, N.Y.) supplemented with 1 mM L-glutamine 1% penicillin/streptomycin, 0.01 M HEPES, and 1% heat-inactivated normal mouse serum. Stimulator spleen cells were obtained from normal male C57BL/6 mice, irradiated with 4000 rad of gamma irradiation, washed with Hank's balanced salt solution, and resuspended in culture media. $5 \times 10^5$ responder cells were added to $5 \times 10^5$ stimulator cells or media alone in a total volume of 0.2 ml in 96 well flat-bottomed plates. After 96 hr, cell proliferation was assayed by incubation with 1 µCi of $^3$H-thymidine (New England Nuclear, Boston, Mass.) and, after an additional 18 hours, cells were harvested and counted in a scintillation counter. Cell suspensions from each animal were assayed in sextuplicate and expressed as the mean +/– SEM of 3–6 mice per group. FIG. 2 shows a representative experiment of three separate experiments.

Figure 3:
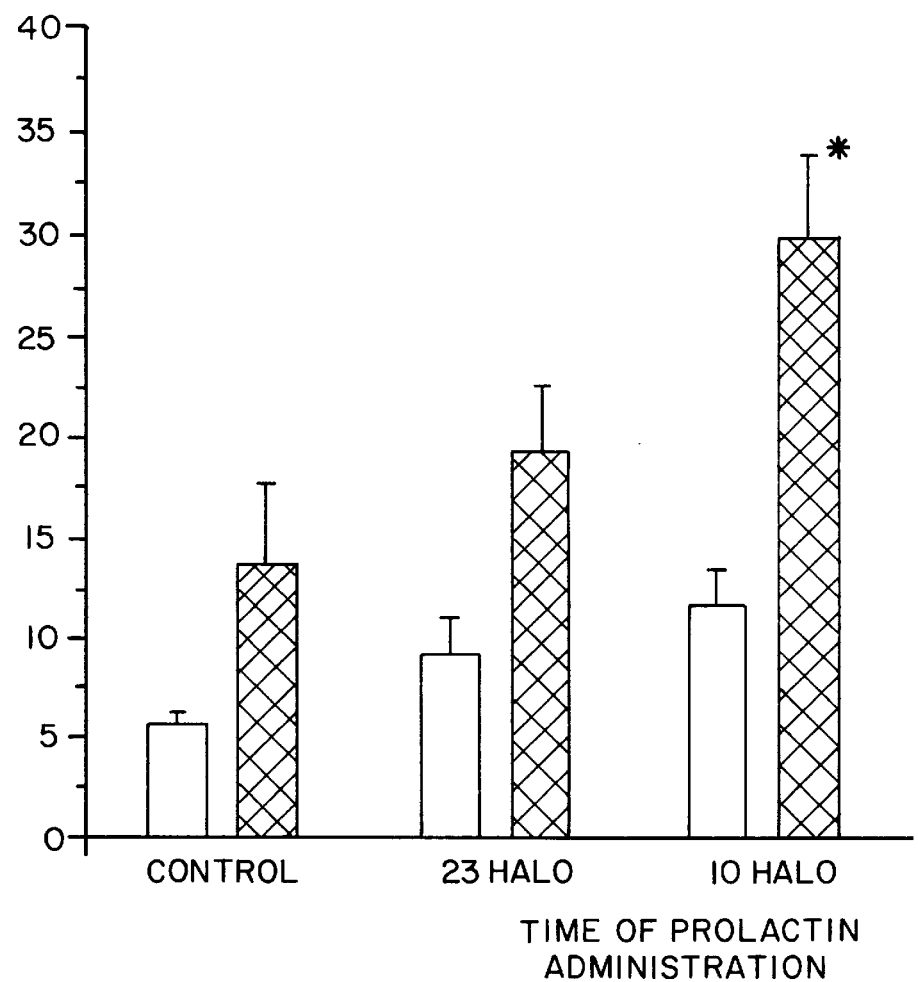

As can be seen by reference to FIG. 3, prolactin injections made 4–12 HALO substantially increased (114%, p<0.05) MLR response to alloantigens. Also increased (to a lesser albeit still significant extent) was the proliferation of non-stimulated responder splenocytes from treated animals as compared to the negative controls. It should be noted that injections made 16–20 HALO had no significant effect on MLR response. Additionally, injections at light onset (0/24 HALO) resulted in a 66% inhibition of MLR compared to controls.

Thus, the experiment of this example illustrates dramatically the importance of timing of increases in prolactin level. Increasing the amount of circulating prolactin at different times causes augmentation of immune response to alloantigen or suppression of immune response to alloantigen or produces no significant effect.

The foregoing results have been repeated in another similar experiment the results of which are shown in FIG. 2 (n=5).

EXAMPLE 2

TIME OF DAY DEPENDENT EFFECTS ON BROMOCRIPTINE ON HAPTEN-SPECIFIC DELAYED-TYPE HYPERSENSITIVITY RESPONSES

Figure 10:
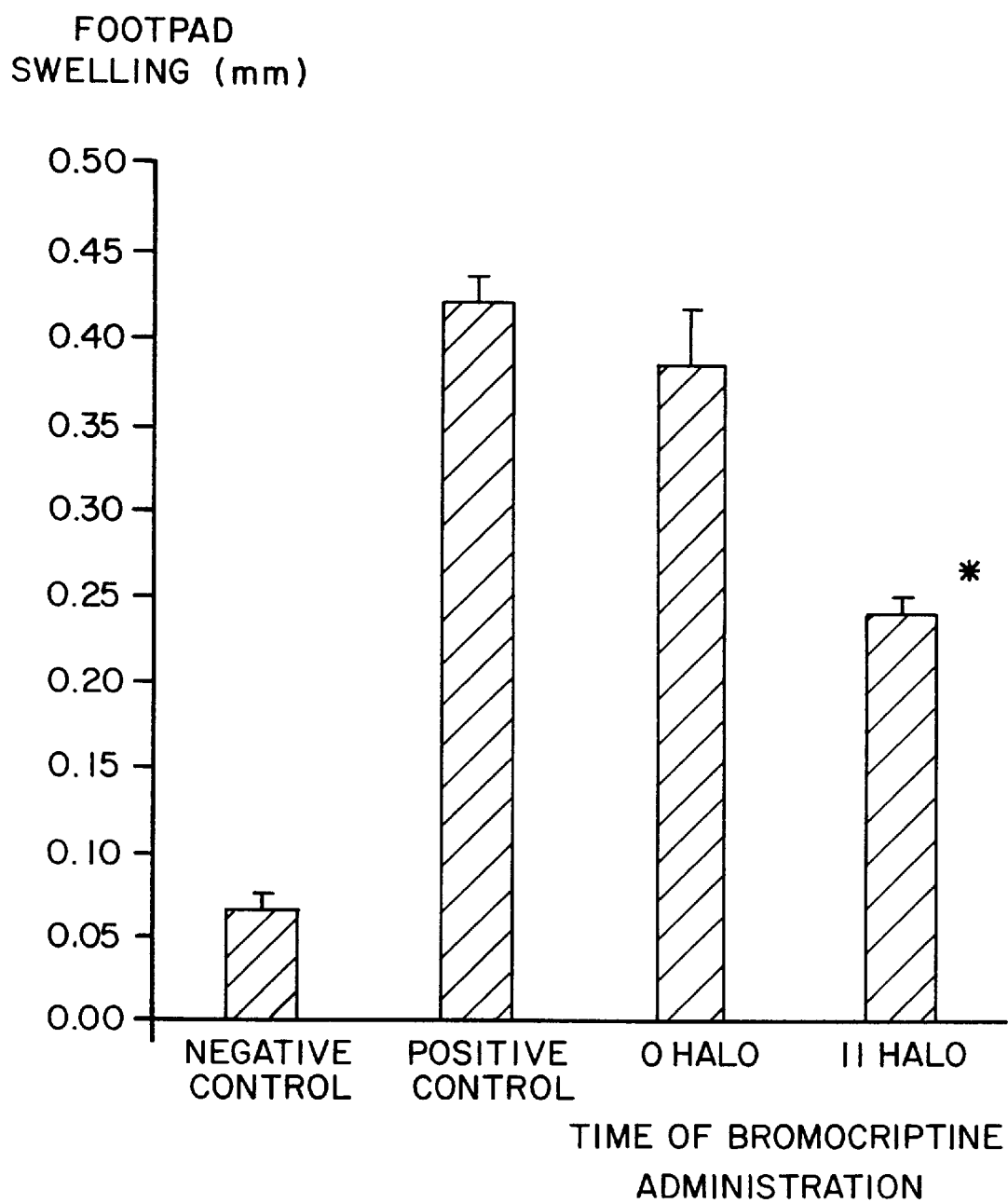
FIG. 10 is the same type of diagram as FIG. 9 but represents the mean percent inhibition of foot pad swelling compared to the positive controls obtained from 4 experiments. An asterisk denotes a significant difference from the positive control in millimeters of foot pad swelling (p<0.008; Student's t test).

Adult male BALB/c mice (5–6 mice per group) maintained on 12 hour daily photoperiods were injected daily for 12 days with bromocriptine at 0.5, 1.5, 2.5, or 5.0 mg/kg body weight at either 0 or 10 HALO. A control group remained untreated. Six days after the initiation of drug treatment, treated and positive control (sensitized but no bromocriptine) mice were sensitized to azobenzene arsonate (ABA) by subcutaneous injection of $3.0 \times 10^7$ ABA-coupled syngeneic male spleen cells (Bach, B. A. et al., *J. Immunol.* 121:1460–1468, 1978). A negative control group remained unsensitized. Six days following sensitization, all mice were challenged in the foot pad with 30 µl of 10 mM ABA solution. Footpads were measured 24 hours later and the swelling response was determined by subtracting the thickness of the non-injected footpad from that of the injected footpad. FIG. 10 represents the mean percent inhibition of footpad swelling compared to the positive controls obtained from 4 experiments.

As can be seen in FIG. 10, different amounts of bromocriptine produced different effects on the immune system depending on the time of their administration. Thus, at 0 HALO, 0.5 mg/kg or 1.5 mg/kg or 2.5 mg/kg of bromocriptine had no significant effect in inhibiting footpad swelling. 5.0 mg/kg of bromocriptine administered 0 HALO produced significant inhibition of DTH responses (i.e. had a significant immunosuppressive effect).

On the other hand, at 10 HALO, dosages of 1.5, 2.5 and 5.0 bromocriptine had a significant suppressive effect. This indicates that the DTH inhibitory (i.e. immunosuppressive) effect of bromocriptine when bromocriptine is given at 10 HALO is much greater than if given at 0 HALO. Bromocriptine inhibits prolactin secretion in mice for about 4–6 hours when administered at 1.5 mg/kg and for about 16 hours when administered at 5 mg/kg. Thus, the 5.0 mg/kg dosage at 0 HALO produced a long-lasting suppression of endogenous prolactin that most likely carried over to the window of immunoresponsiveness to prolactin. These results show that the dosage of prolactin reducer should not be so high as to ablate the daily prolactin level cycle of the treated mammal but should be kept at levels that reduce prolactin substantially only during the desired interval of day. The results of this Example 2 also show that the immune responsiveness to prolactin obeys a daily rhythm. The experiment of this Example 2 also provides a method for determining the appropriate dosage or dosage range for a prolactin modulator.

Figure 9:
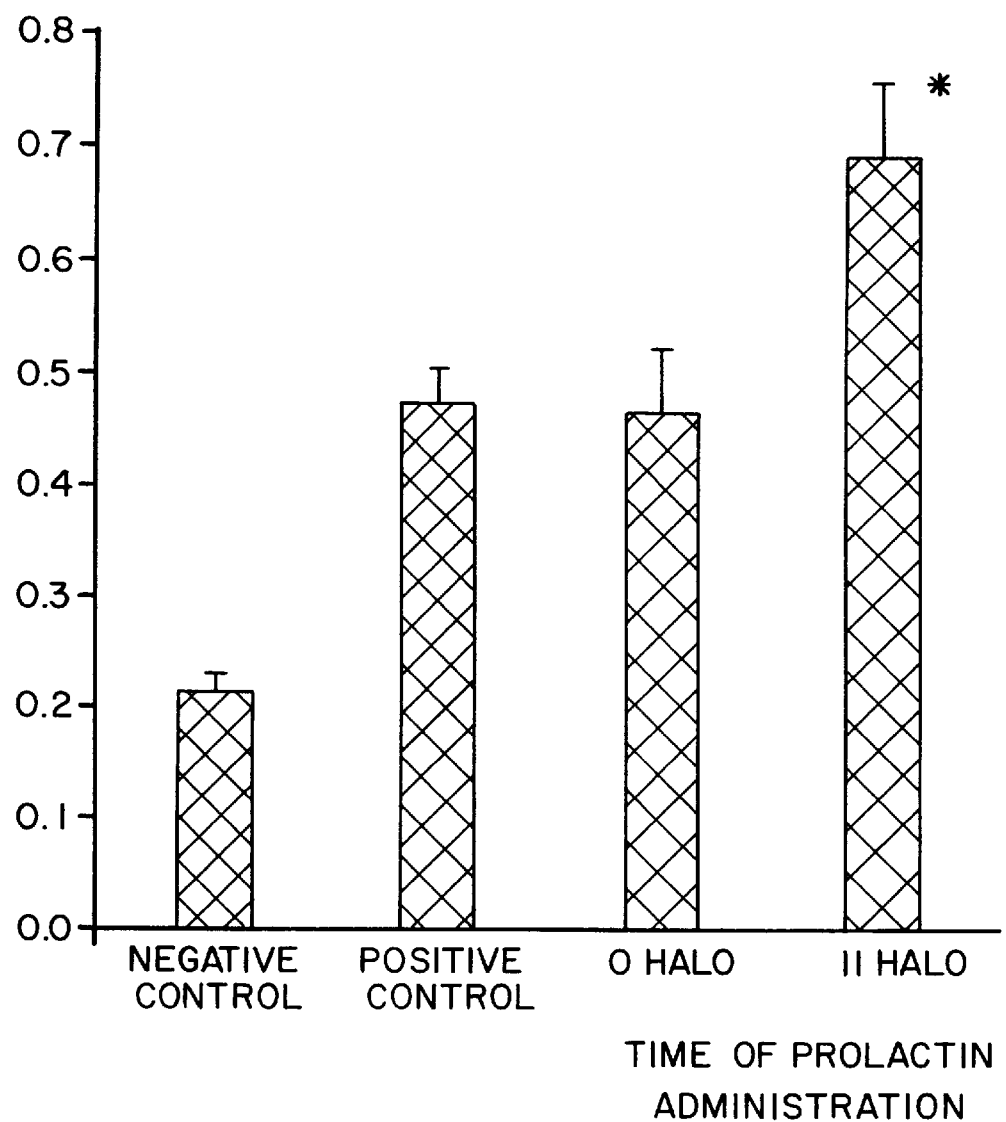
FIG. 9 is a bar diagram showing the relationship between delayed-type hypersensitivity (DTH) responses (foot pad swelling) and time of day of prolactin administration.

The same type of experiment was conducted with prolactin administered at 20 μg per animal per day for 12 days at 0 HALO or at 11 HALO. The DTH response (expressed as foot pad swelling mm) is shown in FIG. 9 compared to negative and positive control. The asterisk denotes a significant difference from positive control.

The foregoing DTH experiments validate the usefulness of the present invention in augmenting and suppressing immune responses, including immune responses to alloantigen (e.g., allograft rejection).

EXAMPLE 3

The MLR experiment of Example 1 was repeated but bromocriptine (200 μg/animal/day or 50 μg/animal/day) was administered for 7 days at 0 and 9 HALO. The results are shown in FIG. 6 (A and B). Bromocriptine (prolactin reduction) was found to have no effect on MLR at 0 HALO but was significantly inhibiting at 9 HALO.

Figure 7:
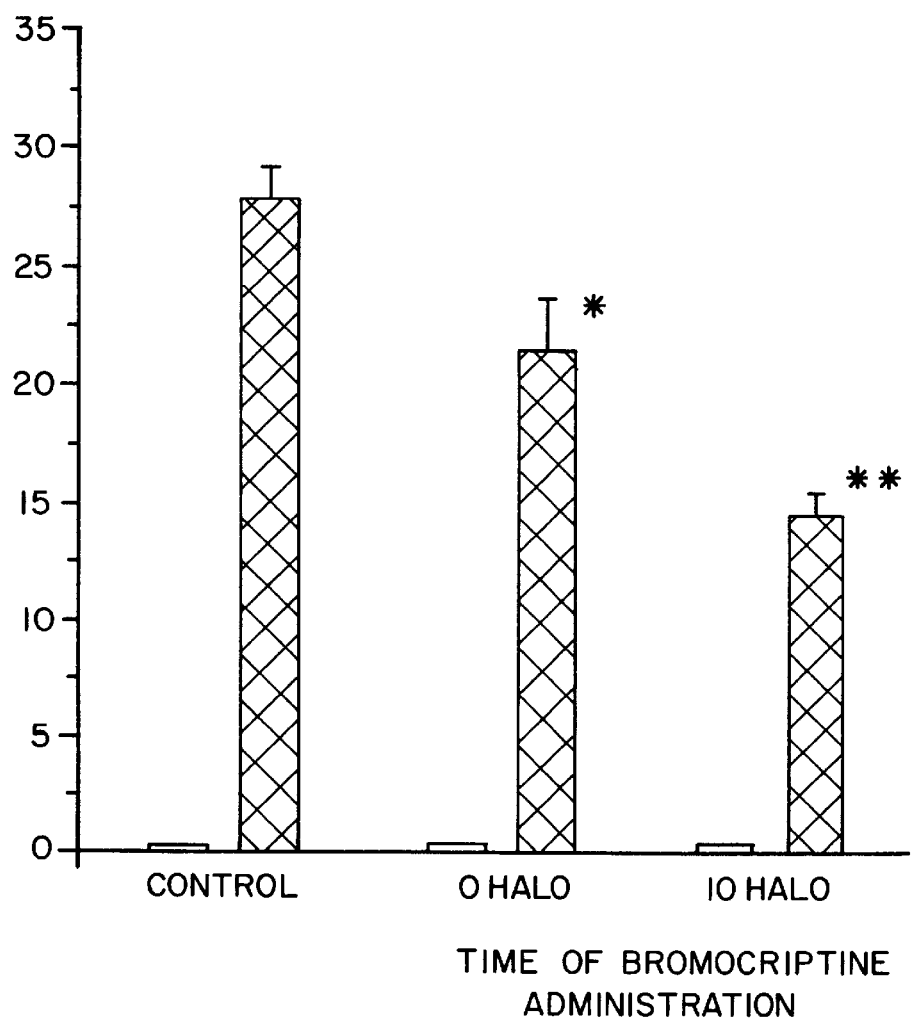
FIG. 7 is a bar diagram showing the relationship between T-cell response to the stimulus Concanavallin A (ConA) and the time of bromocriptine administration.
Figure 8:
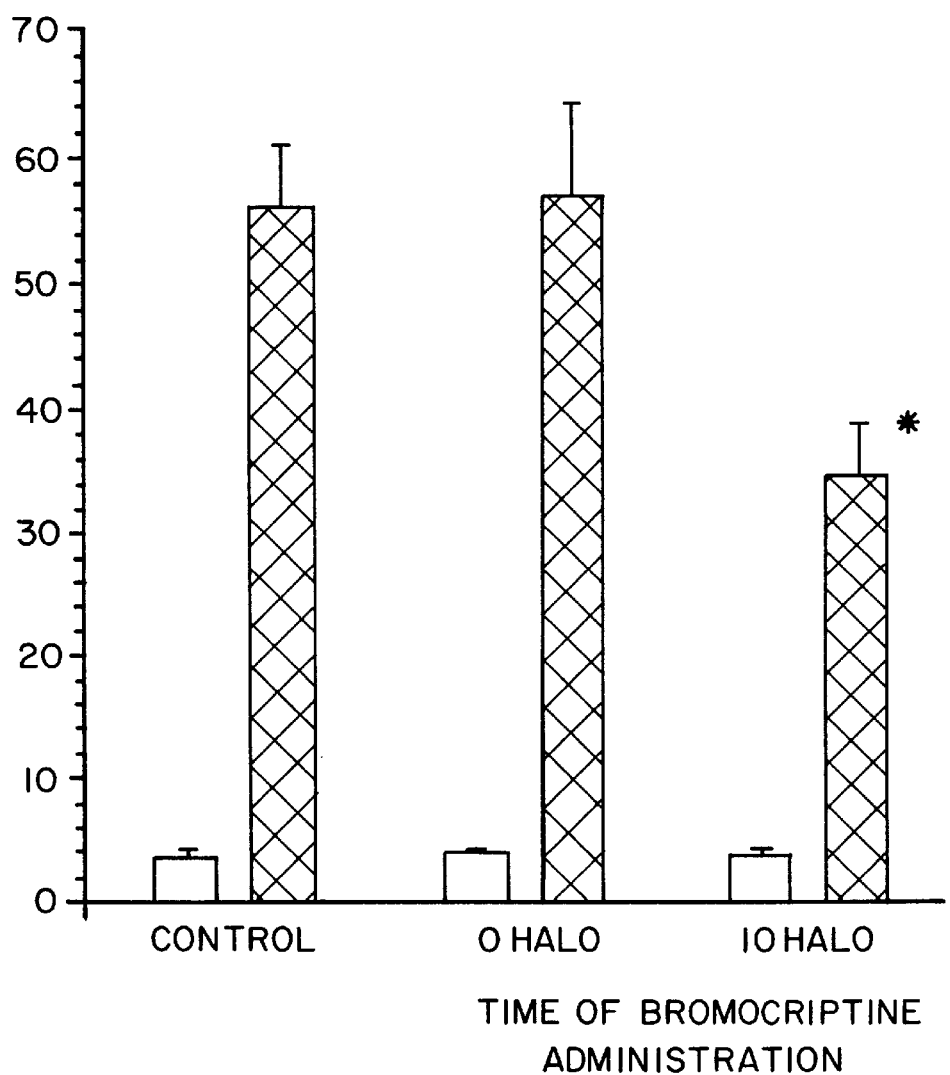
FIG. 8 is the same type of diagram as FIG. 7 but for B-cell response to the stimulus lipopolysaccharide (LPS).

Bromocriptine (50 μg/animal/day for 10 days) was also found to be significantly more inhibitory of both T-cell and B-cell proliferative responses to mitogenic stimulation with either concanavalin A (ConA) in the culture medium (100% inhibition; $p<0.01$) (FIG. 7) or lipopolysaccharide (47% inhibition; $p<0.01$) (FIG. 8) when bromocriptine was administered at 10 HALO as compared to administration of the same amount of bromocriptine at 0 HALO in MLR experiments similar to those of Ex. 1. This supports the existence of a daily rhythm of immune responsiveness to prolactin.

EXAMPLE 4

TIME OF DAY DEPENDENT EFFECT OF PROLACTIN ENHANCERS ON MLR

Figure 4:
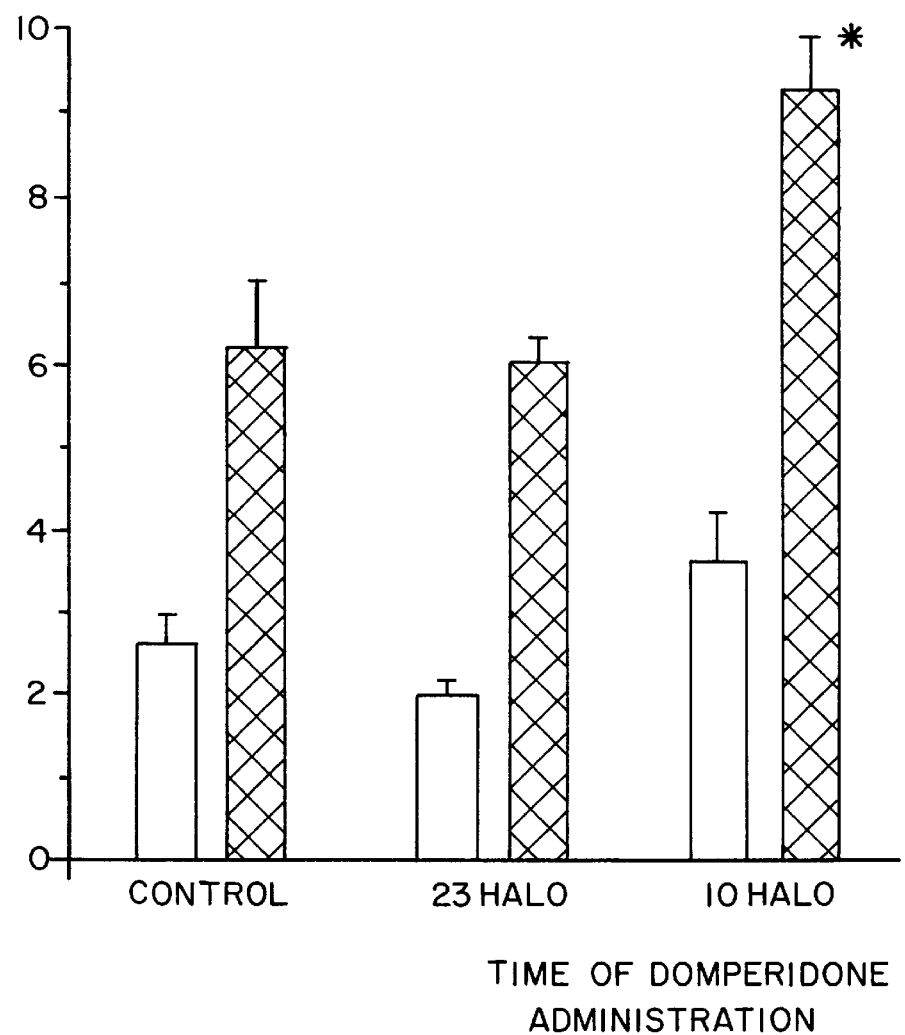
FIG. 4 is the same type of diagram as FIG. 2 but showing the relationship between MLR and time of day of administration of the prolactin-enhancer domperidone.
Figure 5:
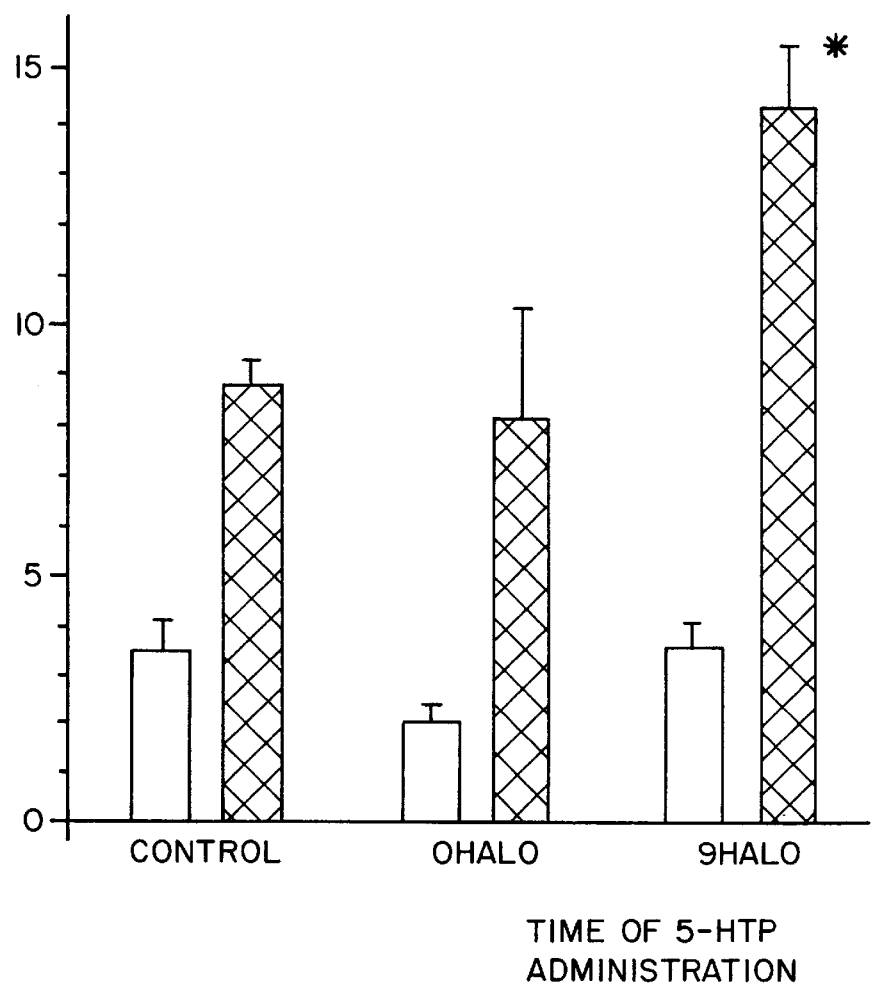
FIG. 5 is the same type of diagram as FIG. 4 but the prolactin enhancer is 5HTP.

The experiment of Example 1 was repeated but the prolactin enhancer domperidone (which does not cross the blood-brain barrier) was administered to mice (n=5 per group) at 23 at 10 HALO to mice in an amount of 1.7 mg/kg/day for seven days. The results, shown in FIG. 4 are that domperidone significantly increased MLR when administered at 10 HALO but not at 23 HALO. The same experiment was conducted with 5-hydroxytryptophane (5HTP) in an amount of 25 mg/kg/day for seven days. Again 5HTP did not change MLR when administered at 0 HALO but significantly increased MLR when administered at 9 HALO. The results are in FIG. 5. These experiments show that prolactin increase can be achieved indirectly by administration of substances that raise circulating (blood) prolactin levels.

EXAMPLE 5

TIME OF DAY DEPENDENT EFFECTS OF PROLACTIN ON THYMUS CELL NUMBER

Adult (5 week old) male BALB/c mice (8–10 animals/group) maintained on 12 hour daily photoperiods were injected daily for 28 days with ovine prolactin (2.25 mg/kg) at 0 or 11 HALO. A control group remained untreated. On day 29 thymuses were removed, cell suspensions were obtained by mechanical dissociation, and total cell number was determined by counting in a hemocytometer chamber. The results of FIG. 11 represent the mean cell number +/− SEM of 8–10 mice per group.

Figure 11:
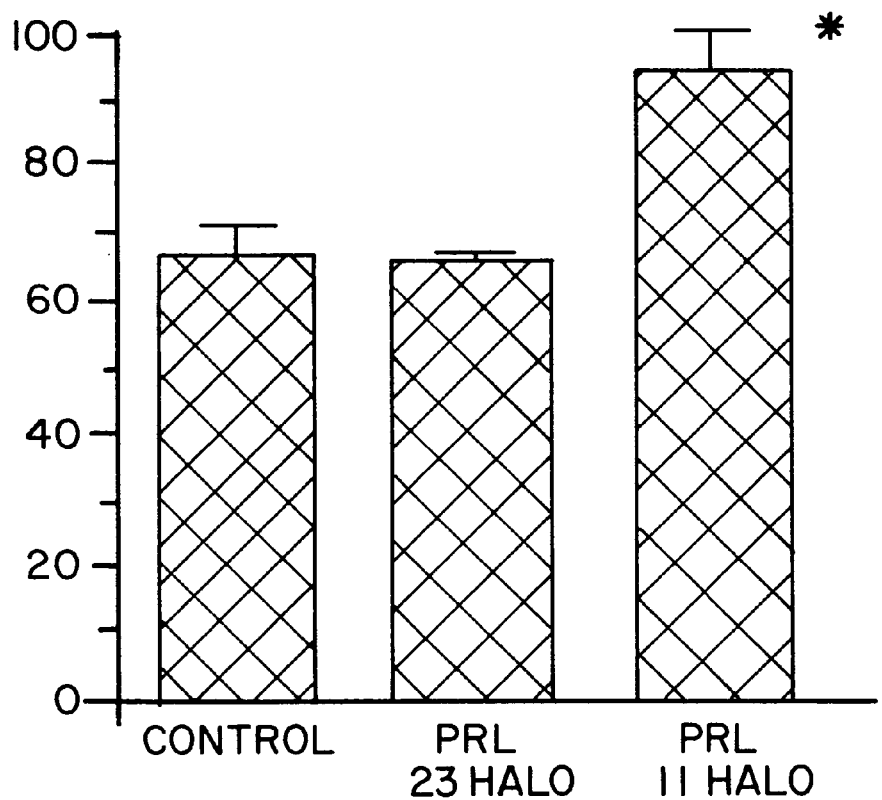
FIG. 11 is a bar diagram showing the relationship between thymus cell number and time of day of prolactin administration in treated and control mice. The results represent the mean cell number +/− SEM of 8–10 mice per group. An asterisk denotes a significant difference from control (p<0.01; Student's t test).

As can be seen in reference to FIG. 11, prolactin treatment at 11 HALO significantly increased to 42% the thymus cell number relative to controls ($p<0.01$) whereas prolactin injections at light onset did not. These results indicate that the stimulatory effect of prolactin on the immune system extends to thymic cells. Additionally, these findings also support that immune responsiveness obeys a circadian rhythm.

In the following Examples 6–10, patients with various autoimmune diseases have been treated with bromocriptine to normalize (or make closer to normal) and reset their daily prolactin profiles. As a result, the immune function of these individuals improved, in that at least one symptom due to inflammation associated with the autoimmune diseases that afflicted each individual was measurably reduced, and/or medication was reduced or discontinued.

EXAMPLE 6

CROHN'S DISEASE

The subject (male; 20 yrs) was diagnosed with Crohn's disease in 1992 based on exploratory surgery and barium X-ray. Approximately 12 inches of the small intestine were inflamed. The subject received prednisone 40 mg/day tapered to zero over a 16 week period.

Figure 12:
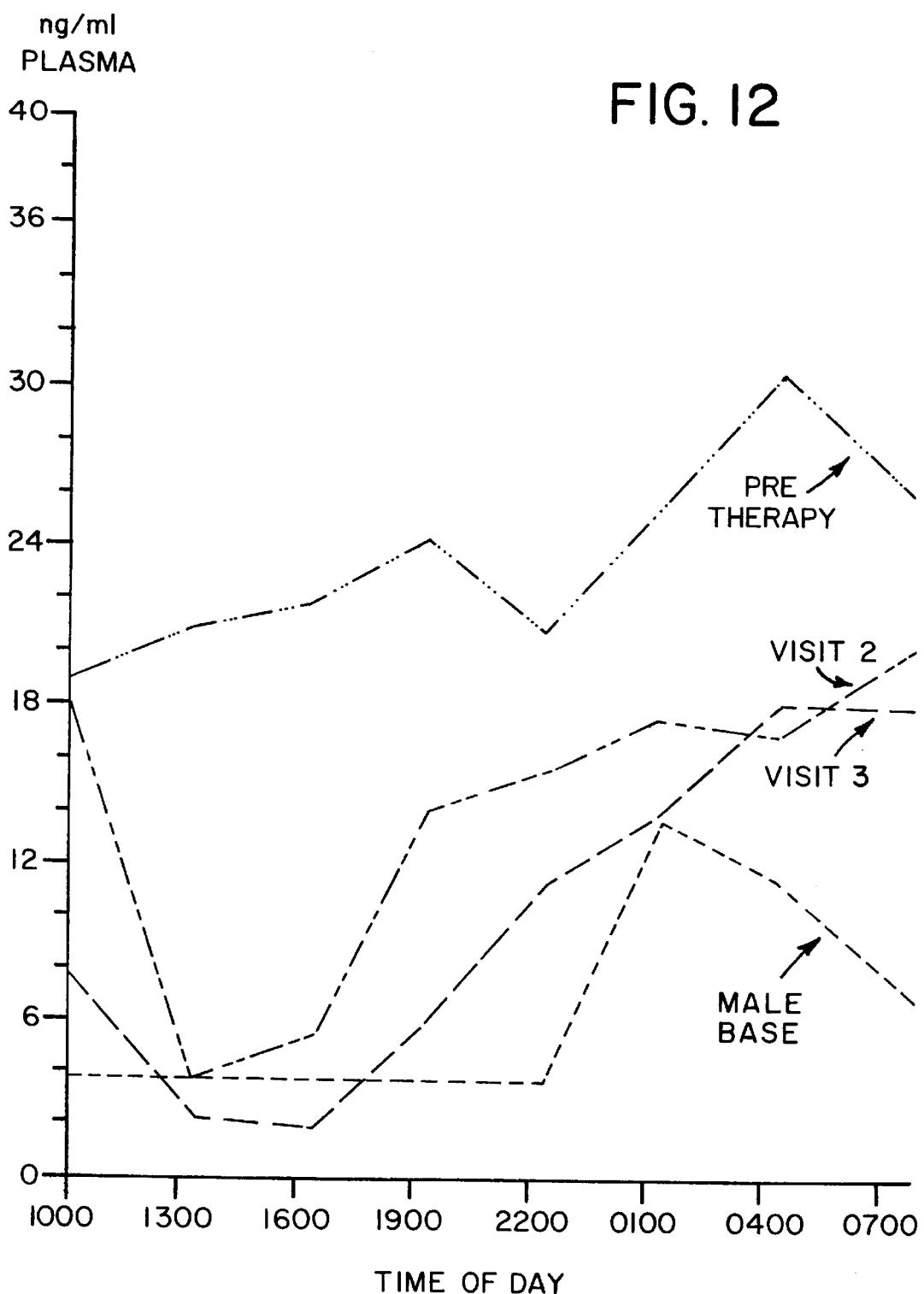
FIG. 12 is a series of tracings depicting the male base prolactin profile (i.e the normal prolactin profile for healthy young males), and, superimposed on it, prolactin level profiles (ng/ml plasma) pre-therapy and in-therapy (visit 2 and visit 3) prolactin profiles for a male patient suffering from Crohn's disease.

The subject's 24-hour pre-therapy prolactin profile (generated about 5 months after he stopped taking prednisone) is shown graphically as the line labelled "pre-therapy" in FIG. 12. It shows prolactin levels that are too high throughout the daytime. The subject was given 1.25 mg of bromocriptine at 08:30 h each day for 20 weeks. A reevaluation profile was generated for this subject after 20 weeks of treatment and is graphically shown as the line labelled "Visit 2" in FIG. 12. (Already at Visit 2, the area under the daytime prolactin curve was substantially reduced which shows progress but prolactin remained too high from 10:00–13:00 and from 16:00–22:00. Ablation of the undesirable early morning peak was also observed.) From this time, the dosage was increased to 2.5 mg per day at 08:30 h to achieve lower prolactin levels during the day. The effects of this change in dosage upon the further prolactin profile of the patient (generated 10 months after the commencement of the 2.5 mg administration) are shown in the line labelled Visit 3 in FIG. 1, which shows that the daytime male prolactin levels of the subject were between 2 and 7 ng/ml for most of the daytime period (07:00–22:00) and its prolactin profile has approached the standard profile in the daytime.

At 15 months from commencement of therapy, the subject still did not have a proper night time peak although daytime prolactin levels remained clearly improved. Bromocriptine therapy was continued at 2.5 mg/day for a further 24 weeks (total therapy 20 months).

The clinical improvements to this patient included: (1) avoidance for surgical resection within this time period (3 yrs. ); (2) no increase in inflamed area of intestine despite discontinuance of prednisone for 2 years, based on a comparison of X-rays from first diagnosis with most recent (post-therapy); (3) during the time from first diagnosis to end of treatment scarring was minimal as determined by intestinal response to prednisone treatment; and (4) the patient reported no major intestinal discomfort during bromocriptine treatment despite no major dietary changes from pre-diagnosis.

EXAMPLE 7

RHEUMATOID ARTHRITIS

The subject (female; 55 yrs old; 5 ft 2 in.; 171.25 lbs) presented with:

(a) rheumatoid arthritis diagnosed in 1972; bursitis in the neck was diagnosed in 1992; symptoms included degeneration of the bones in the fingers; medication: 1800 mg of ibuprofen daily (since October 1992) reduced to 400 mg of ibuprofen (ADVIL) twice daily during bromocriptine treatment and discontinued entirely after 12 weeks of treatment.

(b) obesity: 136% IBW (based on the standard table of Metropolitan Life Insurance Co. NY, N.Y. available from the company)

Figure 13:
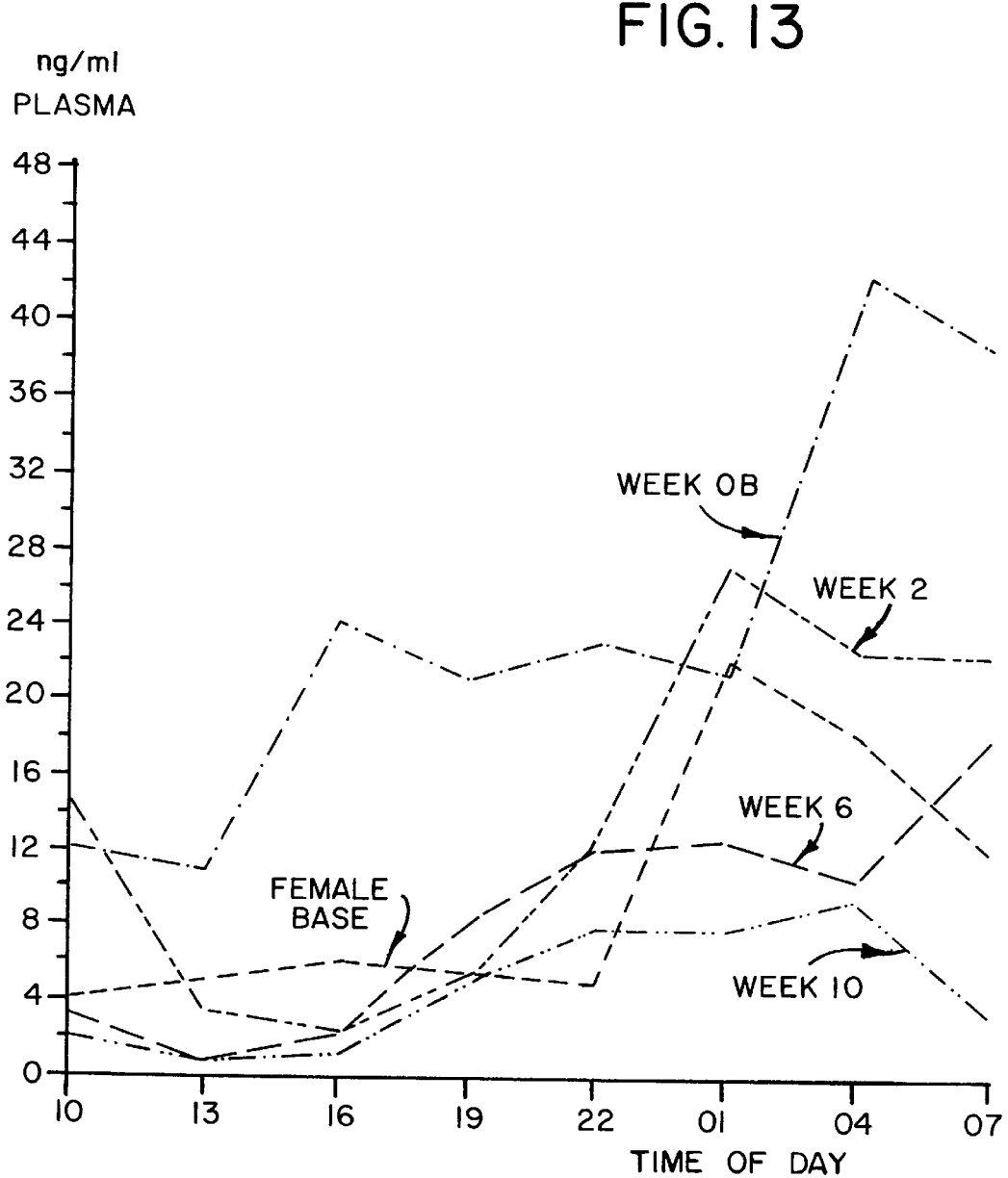
FIGS. 13 and 14, respectively contain the female base prolactin profile and tracings similar to those of FIG. 12 for two female rheumatoid arthritis patients.

The subject's 24 hour pre-therapy prolactin profile is shown graphically in FIG. 13 as the lined labelled "OB". The subject's prolactin level was too high throughout the day, particularly at 07:00 h. In addition, the night time peak was shifted forward. The subject was given 1.6 mg of bromocriptine at 09:00 for the first two weeks and for the following four weeks, the subject was given 0.8 mg of bromocriptine at 05:00 and 1.6 mg of bromocriptine at 09:00. For the next four weeks (weeks 6–10 of the study), the time of the dosage of 1.6 mg of bromocriptine was changed from 09:00 hr to 10:00 hr. Re-evaluation profiles were generated for this patient after 2, 6 and 10 weeks.

The improvements observed in the prolactin profile of this patient after two weeks consisted of prolactin levels throughout the afternoon and early evening that were normalized or very close to normal. However, the prolactin level was still too high at 07:00. The patient's total dosage was increased beginning with week 3, to include 0.8 mg of bromocriptine at 05:00 hr, in an attempt to lower the patient's prolactin level at 07:00 h. Indeed, the patient's prolactin level at 07:00 hr was reduced to near normal after six weeks of treatment. Therapy lasted 18 weeks. As can also be seen in FIG. 13, after 10 weeks of treatment the daytime prolactin level of the patient remained normal but the night time prolactin level was reduced below normal levels. Based on substantial clinical experience in prolactin rhythm modifications, however, the inventors believe that a patient afflicted with autoimmune disease whose prolactin daytime levels have been normalized (or made closer to normal) benefits from the therapy even though night time levels may still be or may have become abnormal. The present inventors believe that the benefits to this patient will be further increased when the night time levels are also normalized.

The clinical improvements in this patient included: cessation of all arthritis medication after week 12 of the treatment and disappearance of the following symptoms: swelling, pain and stiffness in the joints; and a loss of body fat of approximately 20 pounds, from 65 pounds to 45 pounds. The patient's total weight also dropped over the course of the study by 25 lbs. An additional important clinical benefit to this patient was that the clinical improvements described above have thus far persisted for 8 months following cessation of the treatment.

EXAMPLE 8

RHEUMATOID ARTHRITIS

The subject (female; 46 yrs old; 5 ft. 5.7 ins; 235 lbs) presented with:

(a) rheumatoid arthritis for approximately six years; the patient was taking both naproxen (1500 mg) and aspirin (680 mg) daily, as well as ibuprofen (200 mg) as needed.

Figure 14:
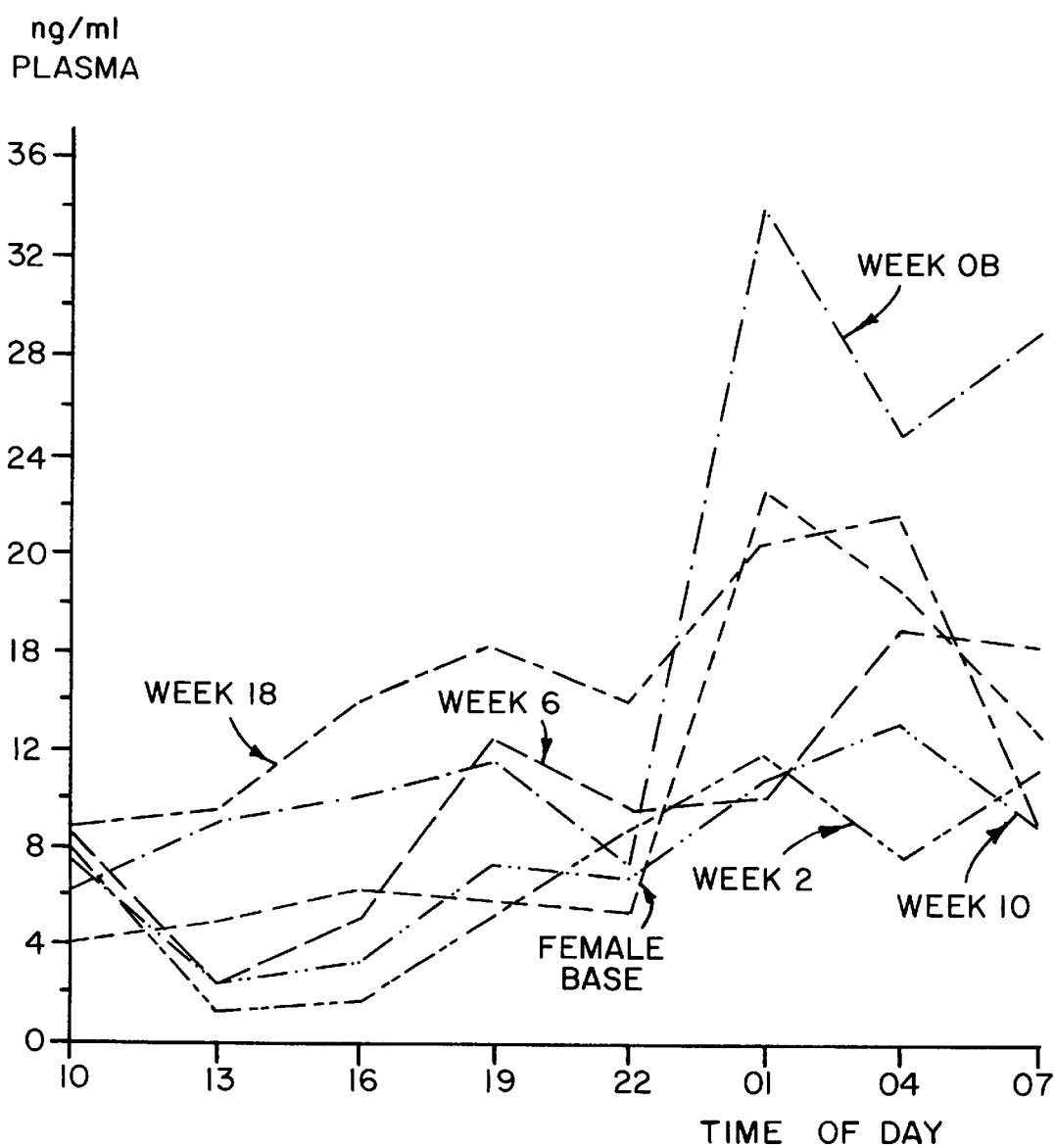

(b) obesity: 156% IBW (based on the standard table of Metropolitan Life Insurance Co.);

The subject's 24 hour pre-therapy prolactin profile is shown graphically in FIG. 14 as the line labeled "Week OB". It shows that pretreatment prolactin levels (Week O.B.) were too high throughout the day, particularly at 07:00 h. For the first 6 weeks of treatment, the subject was given 1.6 mg of bromocriptine at 09:30. From week six through week ten, the subject was given 0.8 mg of bromocriptine at 05:00 hr and 1.6 mg of bromocriptine at 10:00 hr. From week 10 through week 18, the subject was given 1.6 mg of bromocriptine at 05:00 hr and 0.8 mg of bromocriptine at 10:00 hr. Reevaluation prolactin profiles were taken at several intervals, including after 10 and 18 weeks.

The subject's prolactin profile after 18 weeks is shown graphically in FIG. 14. This graph shows that the patient's daytime prolactin levels have been reduced to normal or near normal throughout most of the day. This graph also shows that the patient lacks a proper night time peak. This patient's profile, however, worsened somewhat after her dosage was changed from week 10 to week 18 in that a peak appeared at 19:00.

Bromocriptine therapy lasted for a total of 18 weeks.

The clinical improvements in this patient included: discontinuance of naproxen (except for one two-week interval during treatment) and substitution of tylenol after 18 weeks of treatment, considerable reduction in or disappearance of the following symptoms: pain, joint swelling and stiffness and a loss of body fat of approximately 15 pounds. These improvements have thus far persisted for approximately four months after cessation of treatment.

EXAMPLE 9

FIBROMYALGIA

The subject: (female; 38 yrs); presented with fibromyalgia. Symptoms included chronic fatigue, stomach disorders and chronic pain in the extremities, including the upper and lower legs. Patient was diagnosed approximately one year before beginning treatment. There were no pre-treatment medications.

Figure 15:
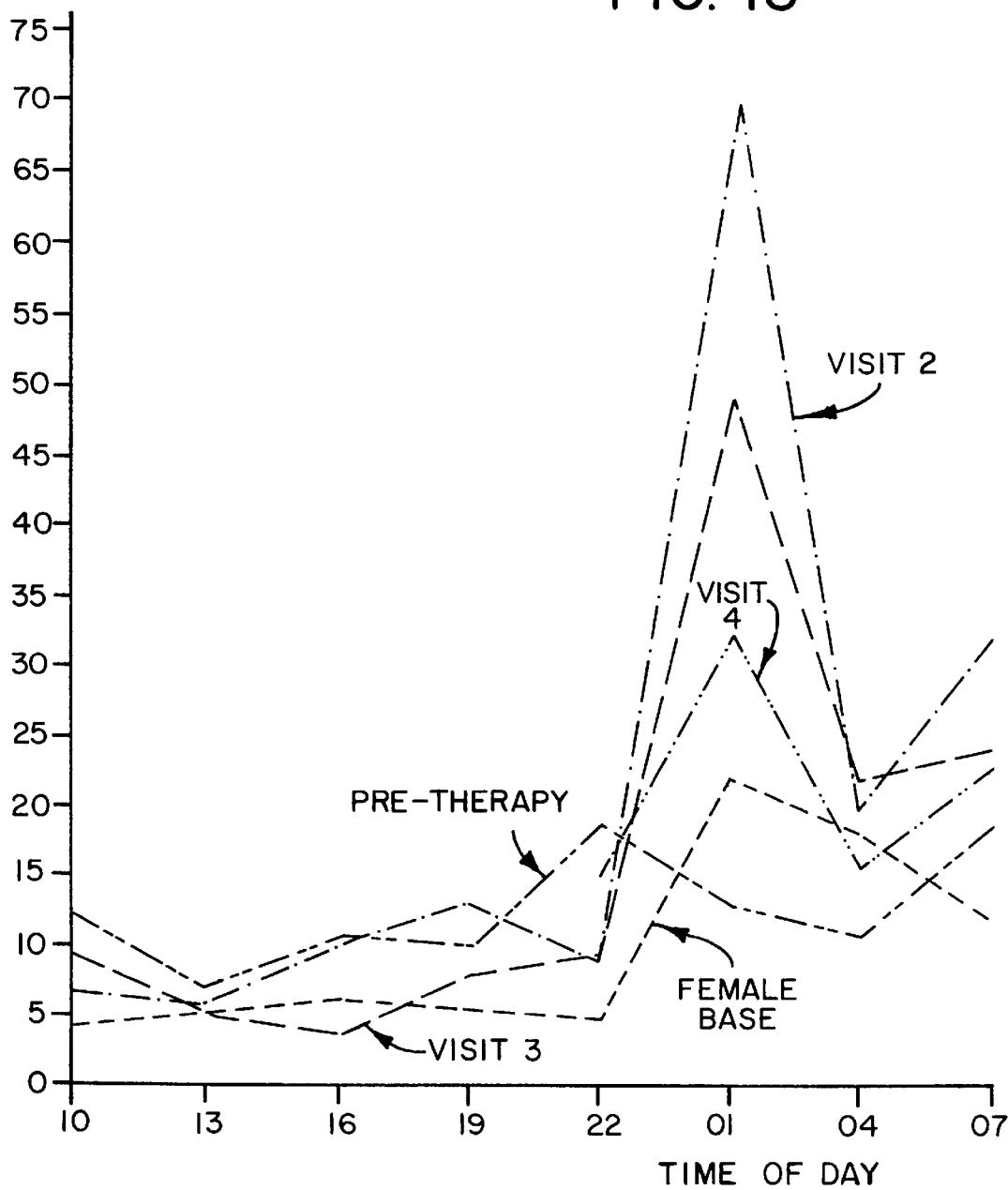
FIGS. 15 and 16, respectively contain the female base prolactin profile and tracings similar to those of FIG. 12 for two female fibromyalgia patients.

The subject's 24 hour base (pre-therapy) prolactin profile is shown graphically in FIG. 15 as the line labeled "pre-therapy". It shows that pre-treatment prolactin levels were moderately elevated during the day and that there was no proper night time peak. Initial dosage of bromocriptine was 0.625 mg at 6:00 am and metoclopramide was 2.5 mg at 10 pm. After four weeks, dosage was changed to 1.25 mg of bromocriptine at 6:00 am and 1.25 mg of metoclopramide at 10 pm. After 8 weeks (4 weeks on the modified dosage) the dosage was not further modified. After 10 more weeks (total 18 weeks) metoclopramide was discontinued but bromocriptine therapy was continued for a further 4 weeks when it was discontinued as the symptoms had virtually disappeared. Reevaluation prolactin profiles were taken at several intervals, including after 17 weeks (visit 3, daytime profile not taken).

The subject's prolactin profile after 4 weeks is shown graphically as the line labeled "Visit 2" in FIG. 15 and the prolactin profile after 17 weeks is shown as the line labelled "Visit 4" in FIG. 15. These graphs show that the patient's daytime prolactin levels have decreased somewhat at certain points of the day and that the patient has a better night time peak.

The clinical improvements in this patient included the disappearance of the following symptoms: chronic fatigue, stomach disorders and chronic pain in the extremities, including the upper and lower legs. These clinical improvements have persisted for approximately 8 months following termination of treatment, which lasted 22 weeks total.

EXAMPLE 10

FIBROMYALGIA

The subject: (female; 27 yrs); presented with fibromyalgia. Symptoms included chronic fatigue, stomach disorders, pain and swelling in all joints, amenorrhea and swelling in the breasts. The patient had been diagnosed approximately five years before beginning treatment. Patient had been taking 650 mg of tylenol (daily) and 16 mg of tylenol with codeine (daily).

The subject's 24-hour base pre-therapy prolactin profile is shown graphically as the line labeled "pre-therapy" in Figure. It shows that prolactin levels are too high throughout the day, particularly at 13:00 hr. For the first 24 weeks of treatment, the patient was administered 0.625 mg of bromocriptine at 08:30. For the following 9 weeks of treatment, the patient was administered 0.625 mg of bromocriptine at 05:30 and 0.625 mg of bromocriptine at 09:30. Reevaluation prolactin profiles were taken at several intervals, including after approximately 24 weeks and 35 weeks of treatment.

Figure 16:
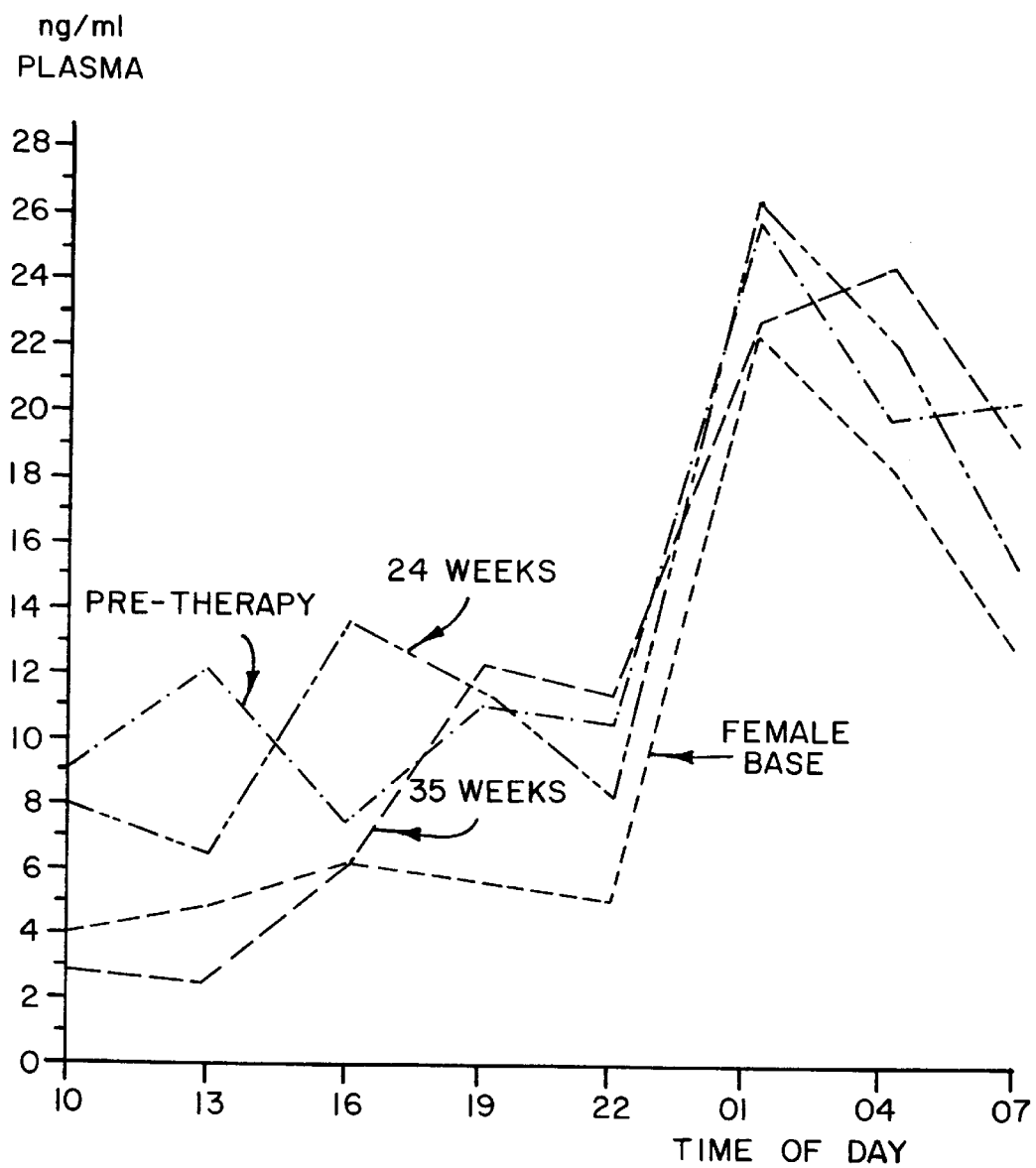

The subject's prolactin profile after 24 weeks is shown graphically as the line labeled "24 Weeks" in FIG. 16. This graph shows that the patient's daytime prolactin levels have been reduced, particularly from 10:00 hr to 16:00 hr. The patient's prolactin level is still somewhat too high in the late afternoon.

The clinical improvements in this patient included: discontinuance of both tylenol and tylenol with codeine, and reduction in the following symptoms: fatigue, stomach disorders and pain in all joints. In addition, a normal menstrual cycle was reinstated and swelling of breasts subsided.

What is claimed is:

1. A method of treating an immune system dysfunction in a mammal suffering from said dysfunction to at least ameliorate said dysfunction comprising administering to said mammal:
 a prolactin reducer only at a time or times predetermined to reduce the mammal's waking hours prolactin levels to cause the mammal's daytime prolactin profile to conform to or approach the standard daytime prolactin profile; and
 a prolactin enhancer only at a time or times predetermined to increase the mammal's night time prolactin levels to cause the mammal's night time prolactin profile to conform to or approach the standard night time prolactin profile.

2. The method of claim 1 wherein said prolactin enhancer is selected from the group consisting of metoclopramide, domperidone, 5-hydroxytryptophan, haloperidol, pimozide, phenothiazine, sulpiride, chlorpromazine, serotonin agonists, pargyline, methadone, estrogens, tryptophan, melatonin, fluoxetine, dexfenfluramine, and non-toxic salts thereof.

3. The method of claim 1 wherein said prolactin reducer is a member selected from the group consisting of bromocriptine, 6-methyl-8-beta-carbobenzy-loxy-aminoethyl-10-alpha-ergoline, an 8-acylaminoergoline, ergocornine, 9,10-dihydroergocornine, a D-2-halo-6-alkyl-8-substituted ergoline, carbidopa, L-dihydroxyphenylalanine, lisuride, and pharmaceutically acceptable acid addition salts thereof.

4. The method of claim 2 wherein said prolactin enhancer is melatonin, said mammal is a human and said melatonin is administered at a predetermined time or times between about 19:00 and 1:00.

5. The method of claim 3 wherein said mammal in need of treatment is a human, said prolactin reducer is bromocriptine, and said bromocriptine is administered at a predetermined time or times between about 05:00 and 13:00.

6. A method for treating an autoimmune disease in a mammal suffering from said autoimmune disease comprising administering to said mammal:
 a prolactin reducer only at a time or times predetermined to reduce the patient's daytime prolactin levels to cause the patient's daytime prolactin profile to conform to or approach the standard daytime prolactin profile; and
 a prolactin enhancer only at a time or times predetermined to increase the patient's night time prolactin levels to cause the patient's night time prolactin profile to conform to or approach the standard night time prolactin profile.

7. The method of claim 6 wherein said autoimmune disease comprises rheumatoid arthritis.

8. The method of claim 6 wherein said autoimmune disease comprises Crohns disease.

9. The method of claim 6 wherein said autoimmune disease comprises lupus erythematosus.

10. The method of claim 7 wherein said prolactin enhancer is selected from the group consisting of metoclopramide, domperidone, 5-hydroxytryptophan, haloperidol, pimozide, phenothiazine, sulpiride, chlorpromazine, serotonin agonists, pargyline, methadone, estrogens, tryptophan, melatonin, fluoxetine, dexfenfluramine, and non-toxic salts thereof.

11. The method of claim 7 wherein said prolactin reducer is a member selected from the group consisting of bromocriptine, 6-methyl-8-beta-carbobenzy-loxy-aminoethyl-10-alpha-ergoline, an 8-acylaminoergoline, ergocornine, 9,10-dihydroergocornine, a D-2-halo-6-alkyl-8-substituted ergoline, carbidopa, L-dihydroxyphenylalanine, lisuride, and pharmaceutically acceptable acid addition salts thereof.

12. The method of claim 8 wherein said prolactin enhancer is selected from the group consisting of metoclopramide, domperidone, 5-hydroxytryptophan, haloperidol, pimozide, phenothiazine, sulpiride, chlorpromazine, serotonin agonists, pargyline, methadone, estrogens, tryptophan, melatonin, fluoxetine, dexfenfluramine, and non-toxic salts thereof.

13. The method of claim 8 wherein said prolactin reducer is a member selected from the group consisting of bromocriptine, 6-methyl-8-beta-carbobenzy-loxy-aminoethyl-10-alpha-ergoline, an 8-acylaminoergoline, ergocornine, 9,10-dihydroergocornine, a D-2-halo-6-alkyl-8-substituted ergoline, carbidopa, L-dihydroxyphenylalanine, lisuride, and pharmaceutically acceptable acid addition salts thereof.

14. The method of claim 12 wherein said mammal is human and said prolactin reducer is bromocriptine administered at a predetermined time or times between about 05:00 and about 13:00.

15. The method of claim 12 wherein said mammal is human and said bromocriptine is administered at a predetermined time or times between about 05:00 and about 13:00.

16. The method of claim 14 wherein said mammal is human and said prolactin reducer is bromocriptine administered at a predetermined time or times between about 05:00 and about 13:00.

17. The method of claim 15 wherein said bromocriptine is administered in an amount in the range of 0.8–8.0 mg/patient/day.

18. The method of claim 16 wherein said bromocriptine is administered in an amount in the range of 0.8–8.0 mg/patient/day.

* * * * *

UNITED STATES PATENT AND TRADEMARK OFFICE
CERTIFICATE OF CORRECTION

PATENT NO. : 6,075,020
DATED : June 13, 2000
INVENTOR(S) : Anthony H. CINCOTTA and Albert H. MEIER It is certified that error appears in the above-indentified patent and that said Letters Patent is hereby corrected as shown below:

On the title page:

[75] Inventors, please correct the address of inventors from "Andover, Mass." to read:

-- Anthony H. CINCOTTA, Tiverton, Rhode Island --

Albert H. MEIER, Baton Rouge, Louisiana --

In line [63] please correct "Continuation of application No. 08/780,727, Jan. 8, 1997, Pat. No. 5,872,127" to read:

-- Continuation of application No. 08/780,727, Jan 9, 1997, Pat. No. 5,872,127

Signed and Sealed this

Seventeenth Day of April, 2001

Attest:

NICHOLAS P. GODICI

Attesting Officer

Acting Director of the United States Patent and Trademark Office